(12) United States Patent
Yugawa

(10) Patent No.: US 10,544,206 B2
(45) Date of Patent: Jan. 28, 2020

(54) ANTIBODY CAPABLE OF BINDING TO NOROVIRUS, COMPOSITE, DETECTION DEVICE AND METHOD USING THE SAME

(71) Applicant: Panasonic Intellectual Property Management Co., Ltd., Osaka (JP)

(72) Inventor: Keiko Yugawa, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/979,950

(22) Filed: May 15, 2018

(65) Prior Publication Data

US 2019/0002535 A1  Jan. 3, 2019

(30) Foreign Application Priority Data

Jun. 30, 2017 (JP) .................. 2017-129719

(51) Int. Cl.
*C07K 16/10* (2006.01)
*G01N 33/569* (2006.01)

(52) U.S. Cl.
CPC ....... *C07K 16/10* (2013.01); *G01N 33/56983* (2013.01); *C07K 2317/565* (2013.01); *C07K 2317/567* (2013.01)

(58) Field of Classification Search
CPC .......... A61K 2039/505; A61K 49/0058; A61K 49/16; C07K 2317/622; C07K 2317/567; C07K 2317/52; C07K 2317/734; C07K 16/462; C07K 16/464
See application file for complete search history.

(56) References Cited

U.S. PATENT DOCUMENTS

2014/0302063 A1  10/2014  Hufton
2016/0102136 A1   4/2016  Bok et al.
2017/0037112 A1   2/2017  Muraoka

OTHER PUBLICATIONS

Adwards et al. Journal of Molecular Biology, 2003, vol. 334, pp. 103-118.*

* cited by examiner

*Primary Examiner* — Bao Q Li
(74) *Attorney, Agent, or Firm* — McDemott Will & Emery LLP

(57) ABSTRACT

The present invention provides a novel antibody capable of binding to a norovirus. The present invention is an antibody that consists of an amino acid sequence, wherein said amino acid sequence consists of, in an N- to C-direction, the following structural domains:

N-FR1-CDR1-FR2-CDR2-FR3-CDR3-FR4-C wherein
FR denotes a framework region amino acid sequence and CDR denotes a complementary determining region amino acid sequence;
the CDR1 consists of any one of an amino acid sequences represented by SEQ ID NO: 1-SEQ ID NO: 6;
the CDR2 consists of any one of an amino acid sequences represented by SEQ ID NO: 7-SEQ ID NO: 12;
the CDR3 consists of any one of an amino acid sequences represented by SEQ ID NO: 13-SEQ ID NO: 17; and
the antibody is capable of binding to a norovirus.

9 Claims, 19 Drawing Sheets

Specification includes a Sequence Listing.

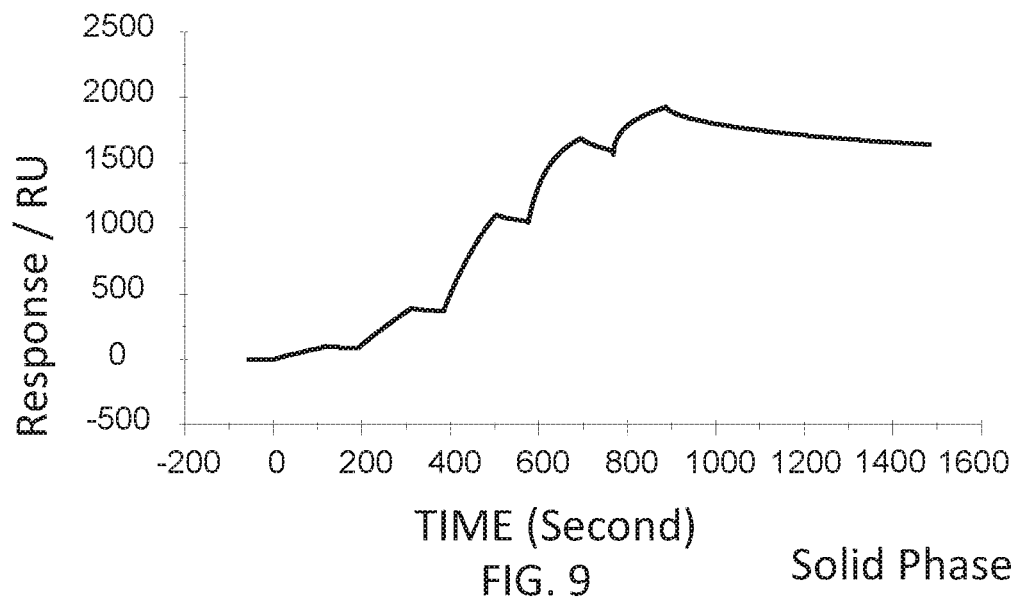
FIG. 9  Solid Phase
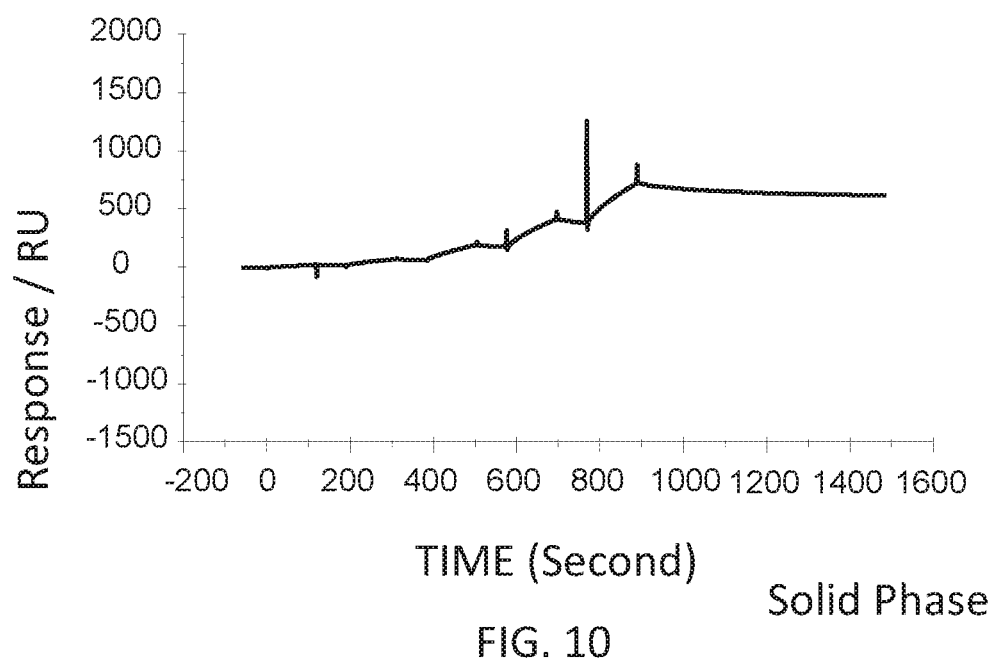
FIG. 10  Solid Phase

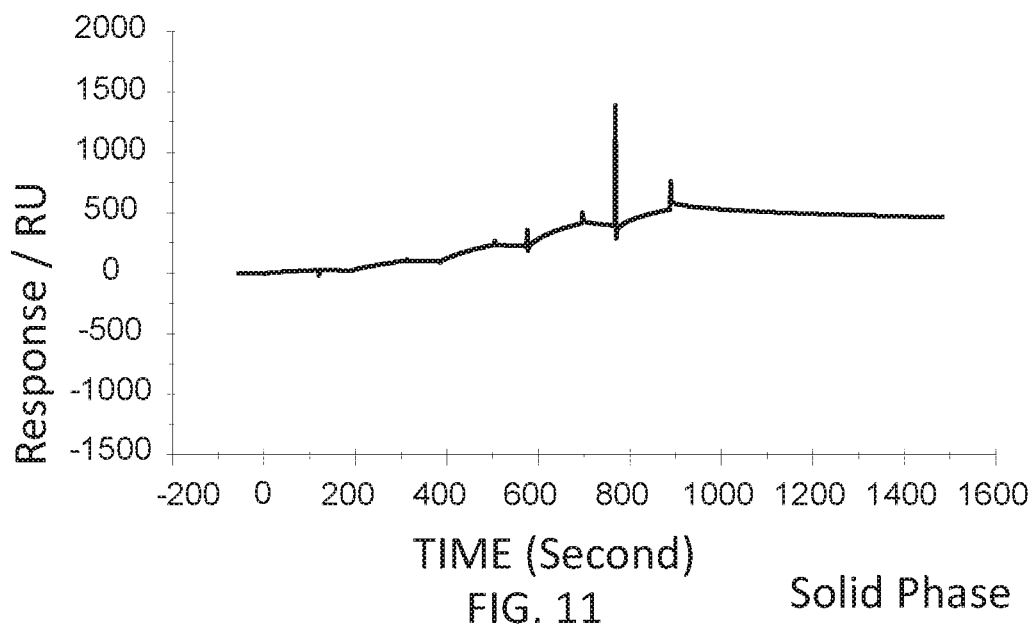
FIG. 11  Solid Phase
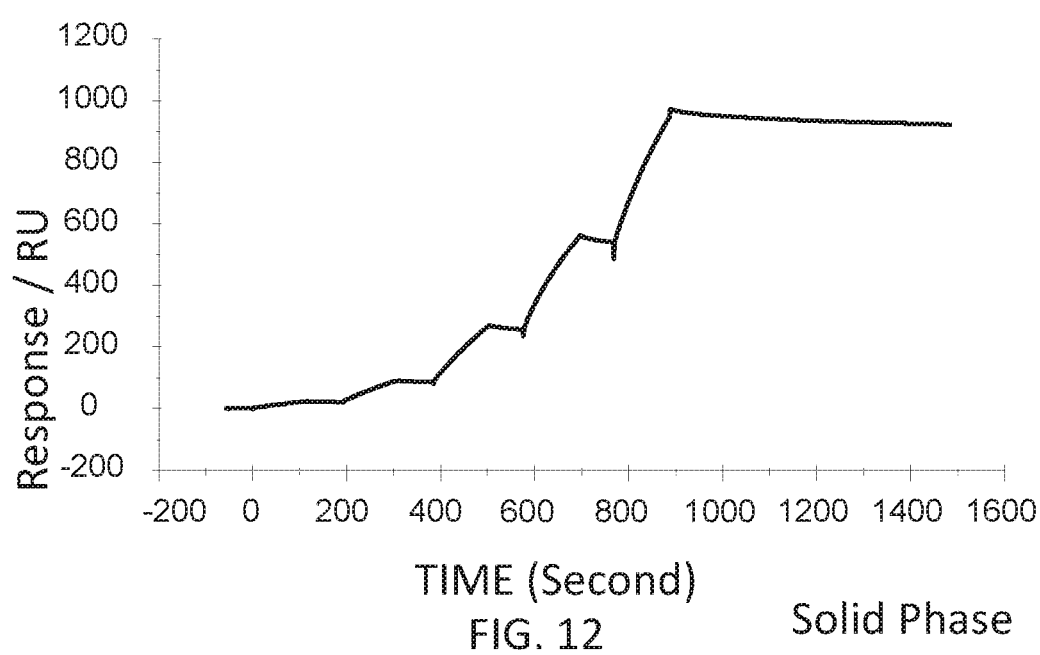
FIG. 12  Solid Phase

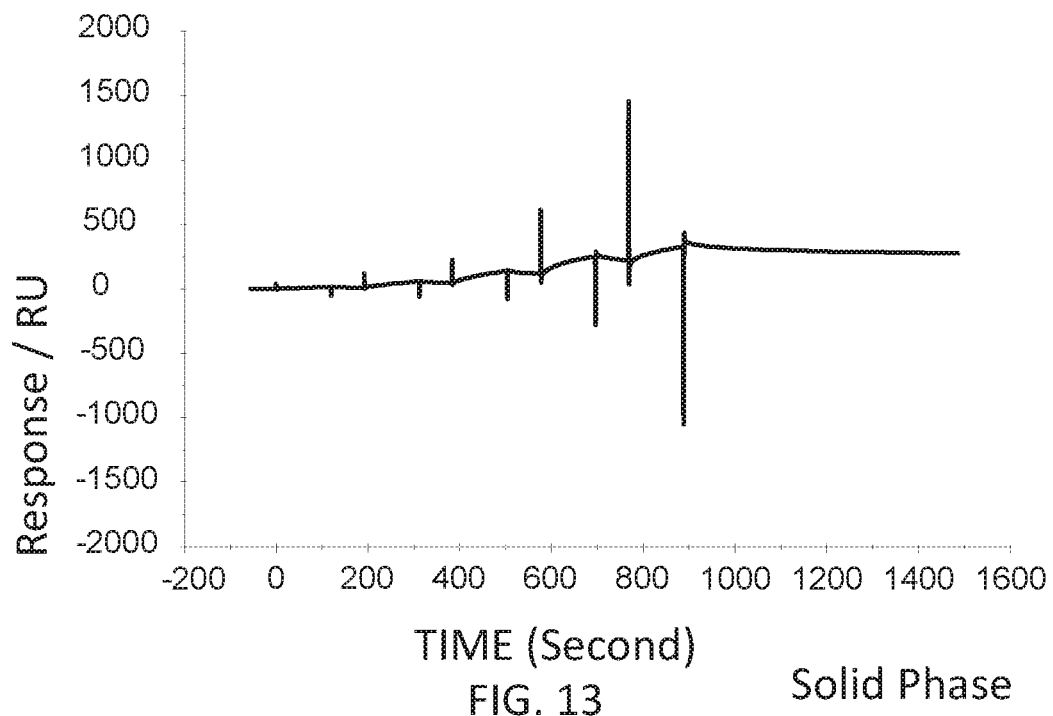
FIG. 13  Solid Phase
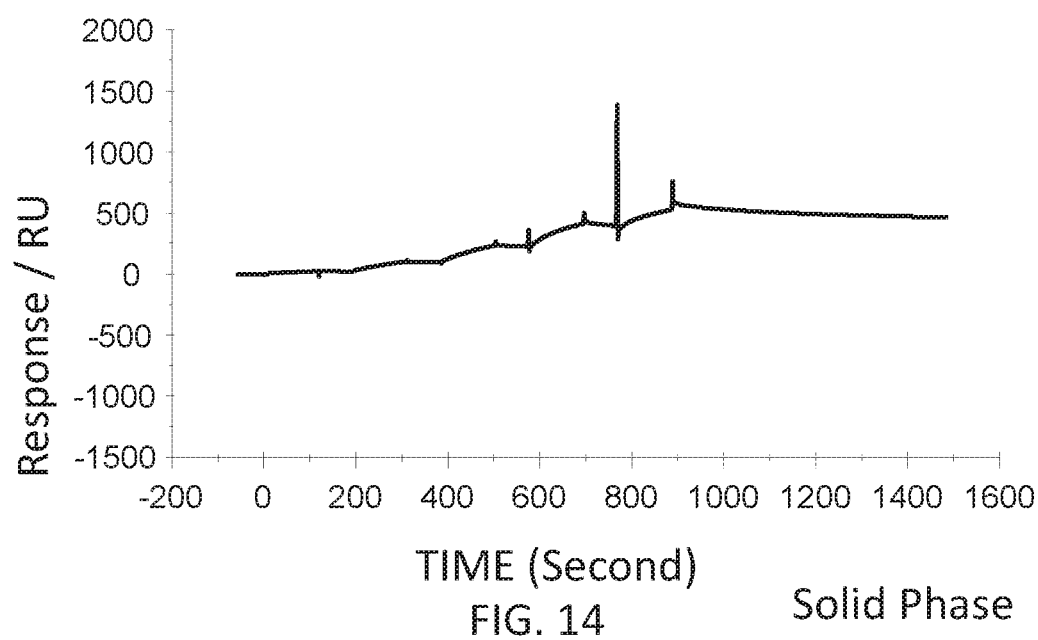
FIG. 14  Solid Phase

ANTIBODY CAPABLE OF BINDING TO NOROVIRUS, COMPOSITE, DETECTION DEVICE AND METHOD USING THE SAME

INCORPORATION BY REFERENCE-SEQUENCE LISTING

The material contained in the ASCII text file named "P1008178US01_ST25.txt" created on May 14, 2018 and having a file size of 41,917 bytes is incorporated by reference herein.

BACKGROUND

1. Technical Field

The present invention relates to an antibody capable of binding to norovirus, a composite, a detection device and a method using the same.

2. Description of the Related Art

Patent Literature 1 discloses antibodies each capable of binding to a norovirus. At least a part of the antibodies disclosed in Patent Literature 1 are derived from an alpaca. Patent Literature 1 is incorporated herein by reference.

CITATION LIST

Patent Literature

Patent Literature 1
United States Patent Application Publication No. 2016/0102136

SUMMARY

An object of the present invention is to provide a novel antibody capable of binding to a norovirus, a composite, a detection device and a method using the same.

The present invention is an antibody including an amino acid sequence, wherein the amino acid sequence includes, in an N- to C-direction, the following structural domains:

N-FR1-CDR1-FR2-CDR2-FR3-CDR3-FR4-C wherein

FR denotes a framework region amino acid sequence and CDR denotes a complementary determining region amino acid sequence;

the CDR1 consists of any one of an amino acid sequences represented by SEQ ID NO: 1-SEQ ID NO: 6;

the CDR2 consists of any one of an amino acid sequences represented by SEQ ID NO: 7-SEQ ID NO: 12;

the CDR3 consists of any one of an amino acid sequences represented by SEQ ID NO: 13-SEQ ID NO: 17; and the antibody is capable of binding to a norovirus.

The present invention provides a novel antibody capable of binding to a norovirus, a composite, a detection device and a method using the same.

31.25 nM) including the amino acid sequence represented by SEQ ID NO: 42 to a norovirus.

Figure 7A:
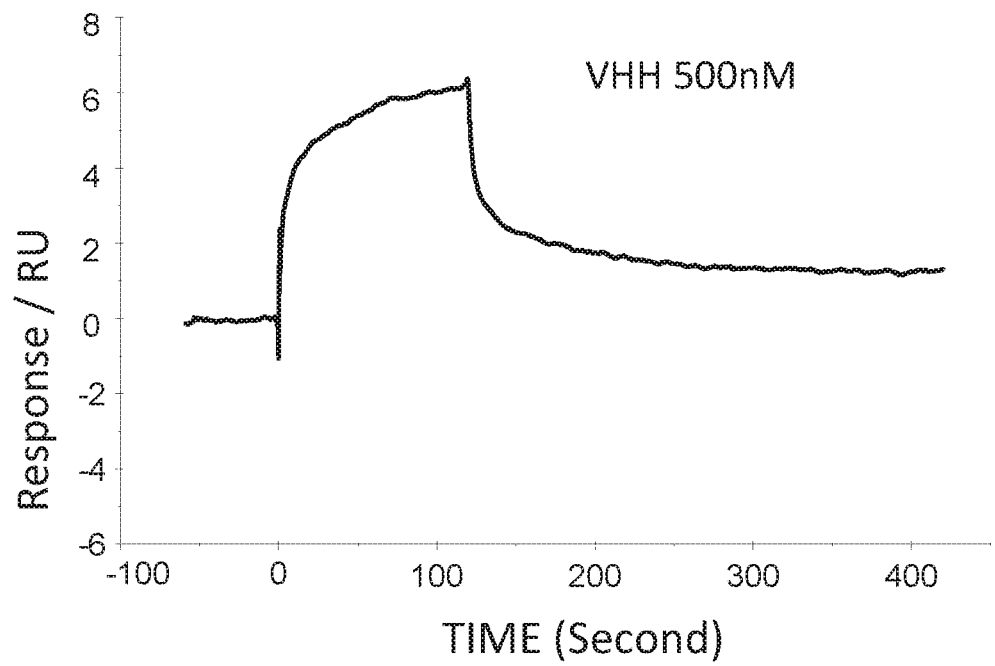
FIG. 7A is a graph showing the SPR evaluation result of the binding ability of the VHH antibody (concentration: 500 nM) including the amino acid sequence represented by SEQ ID NO: 42 to a norovirus.
Figure 7B:
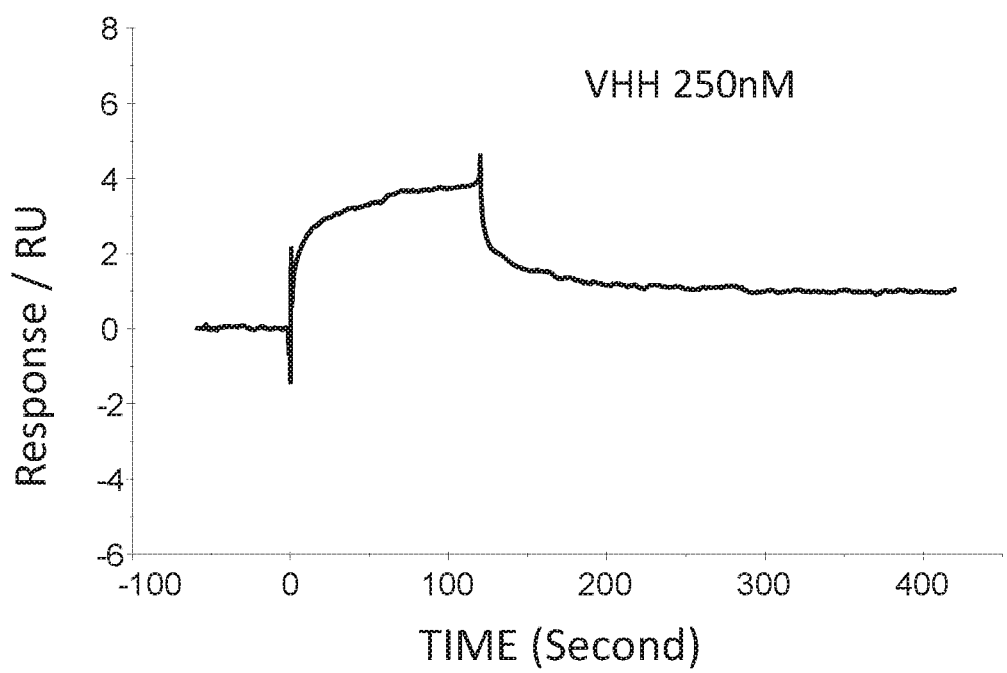
FIG. 7B is a graph showing the SPR evaluation result of the binding ability of the VHH antibody (concentration: 250 nM) including the amino acid sequence represented by SEQ ID NO: 42 to a norovirus.
Figure 7C:
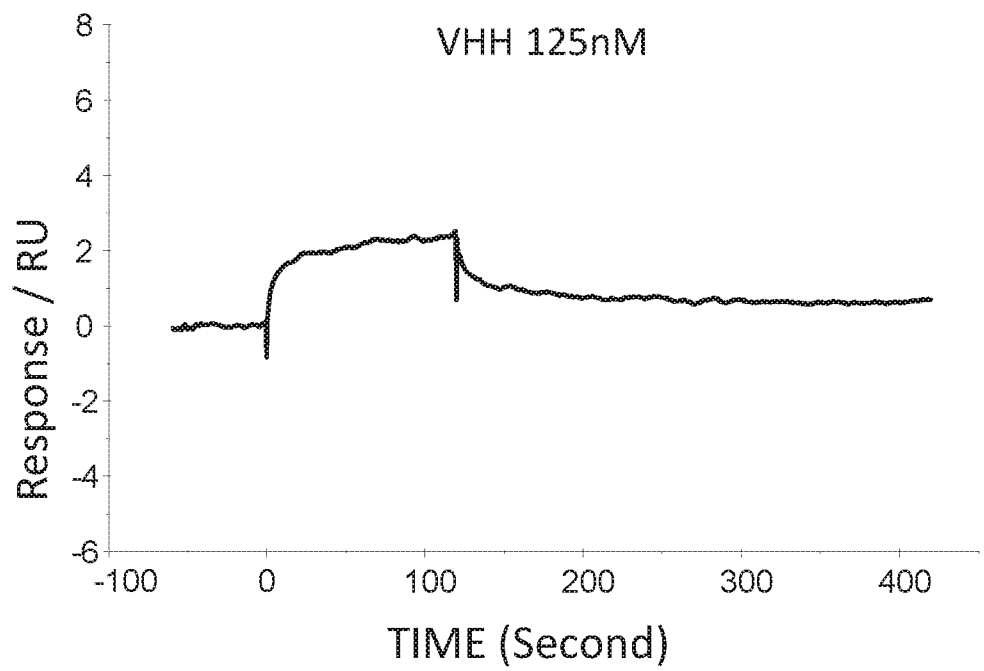
FIG. 7C is a graph showing the SPR evaluation result of the binding ability of the VHH antibody (concentration: 125 nM) including the amino acid sequence represented by SEQ ID NO: 42 to a norovirus.
Figure 7D:
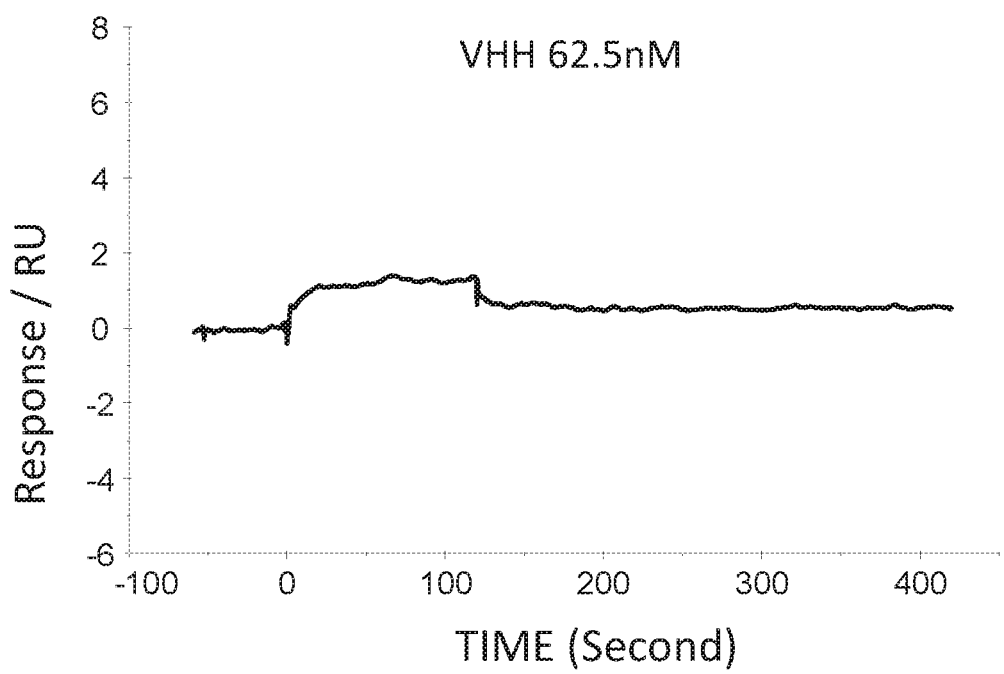
FIG. 7D is a graph showing the SPR evaluation result of the binding ability of the VHH antibody (concentration: 62.5 nM) including the amino acid sequence represented by SEQ ID NO: 42 to a norovirus
Figure 7E:
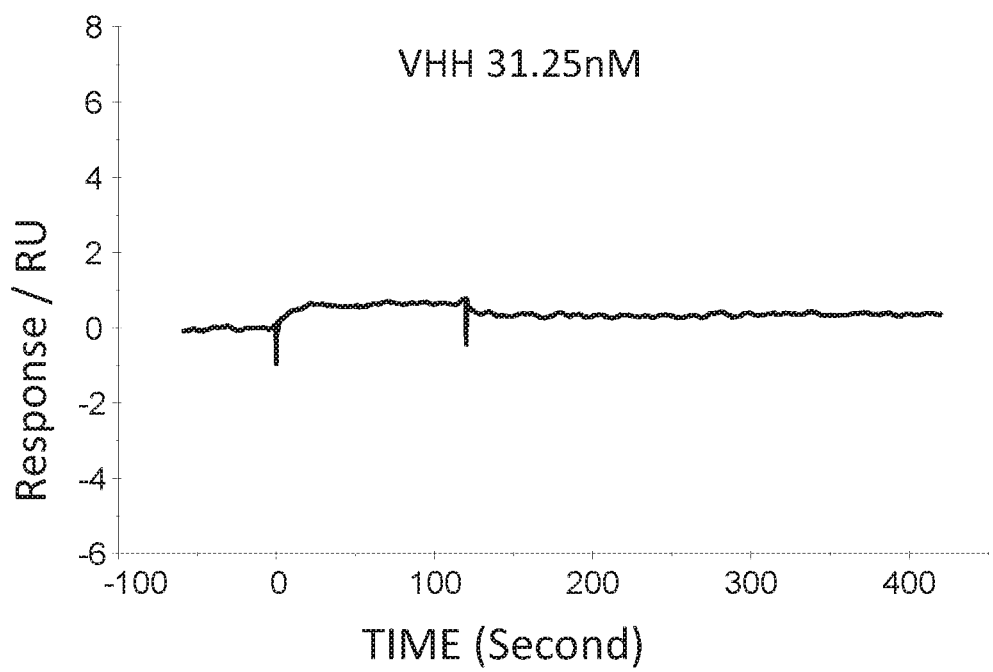
FIG. 7E is a graph showing the SPR evaluation result of the binding ability of the VHH antibody (concentration.
Figure 7F:
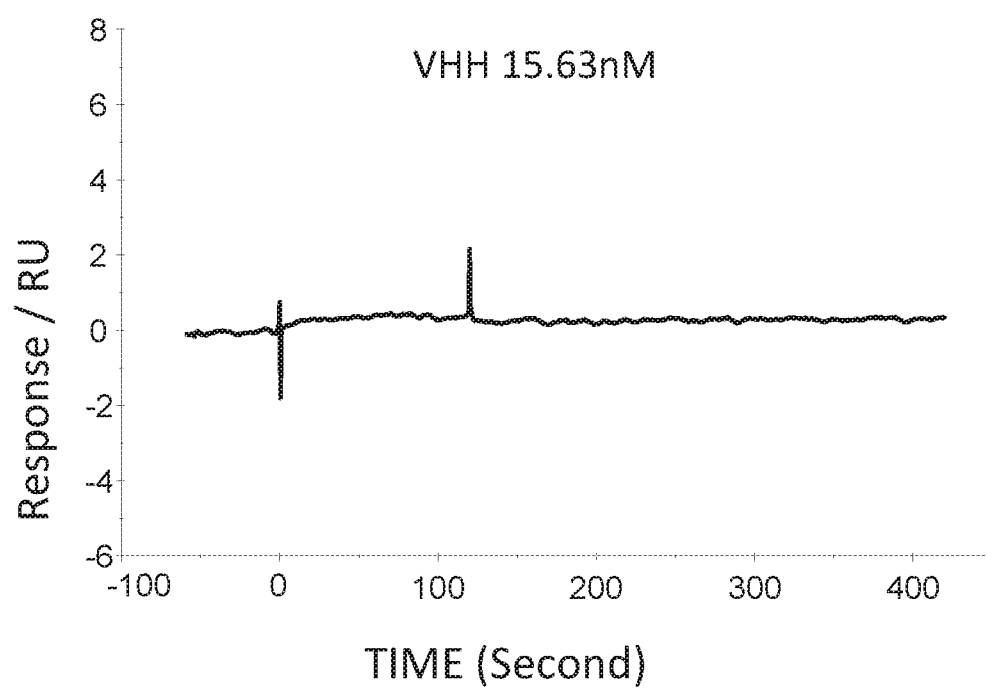

FIG. 7F is a graph showing the SPR evaluation result of the binding ability of the VHH antibody (concentration: 15.63 nM) including the amino acid sequence represented by SEQ ID NO: 42 to a norovirus.

Figure 7G:
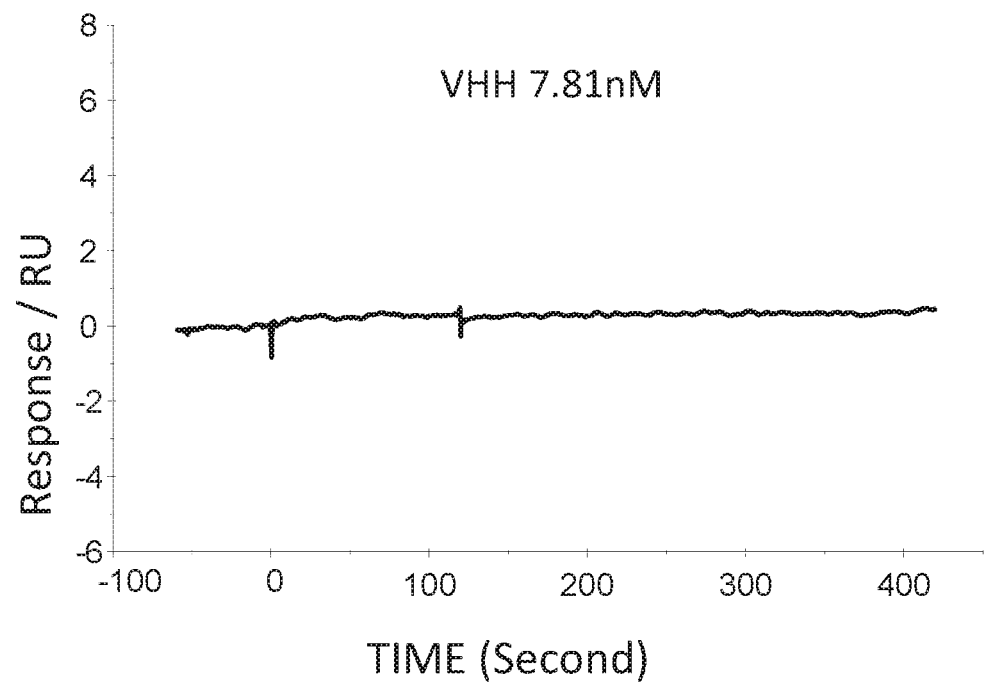

FIG. 7G is a graph showing the SPR evaluation result of the binding ability of the VHH antibody (concentration: 7.81 nM) including the amino acid sequence represented by SEQ ID NO: 42 to a norovirus.

Figure 7H:
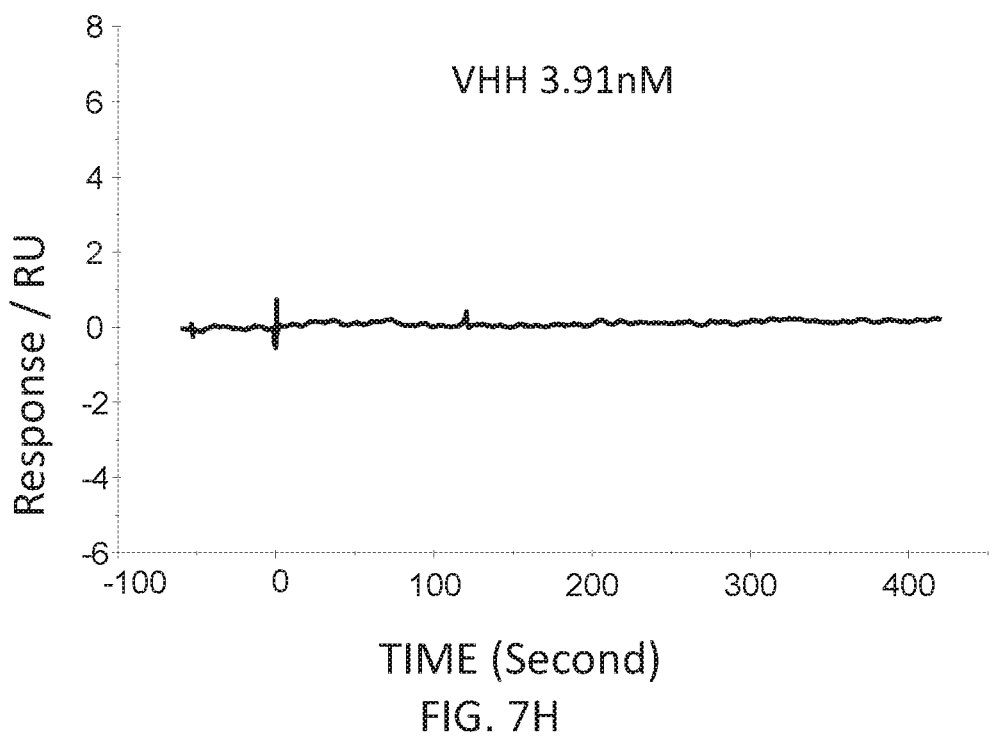

FIG. 7H is a graph showing the SPR evaluation result of the binding ability of the VHH antibody (concentration: 3.91 nM) including the amino acid sequence represented by SEQ ID NO: 42 to a norovirus.

Figure 8A:
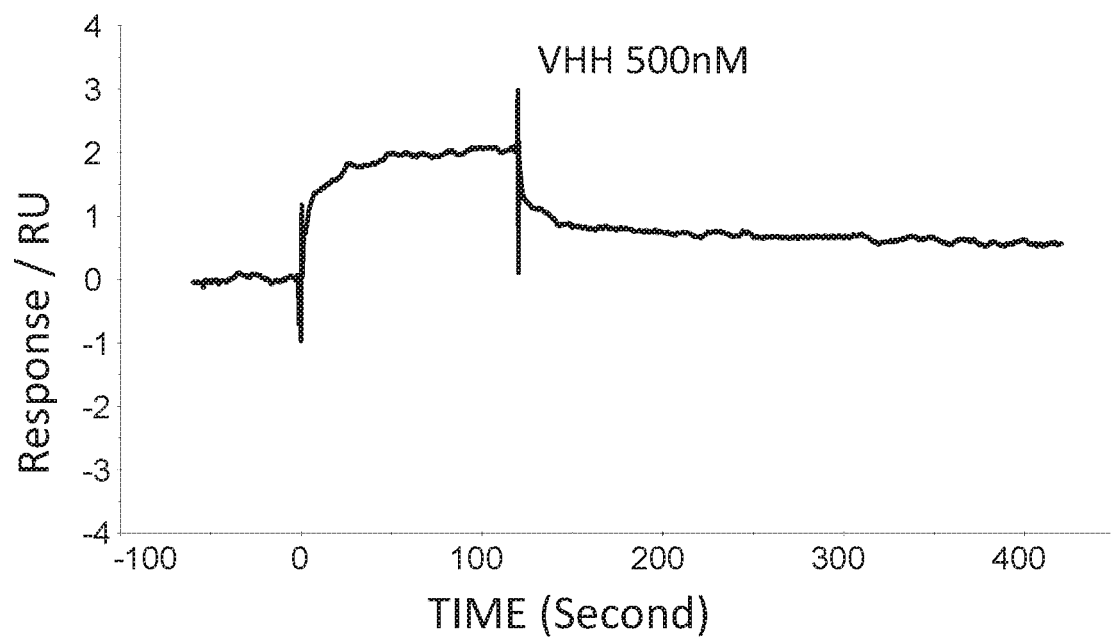

FIG. 8A is a graph showing the SPR evaluation result of the binding ability of the VHH antibody (concentration: 500 nM) including the amino acid sequence represented by SEQ ID NO: 43 to a norovirus.

Figure 8B:
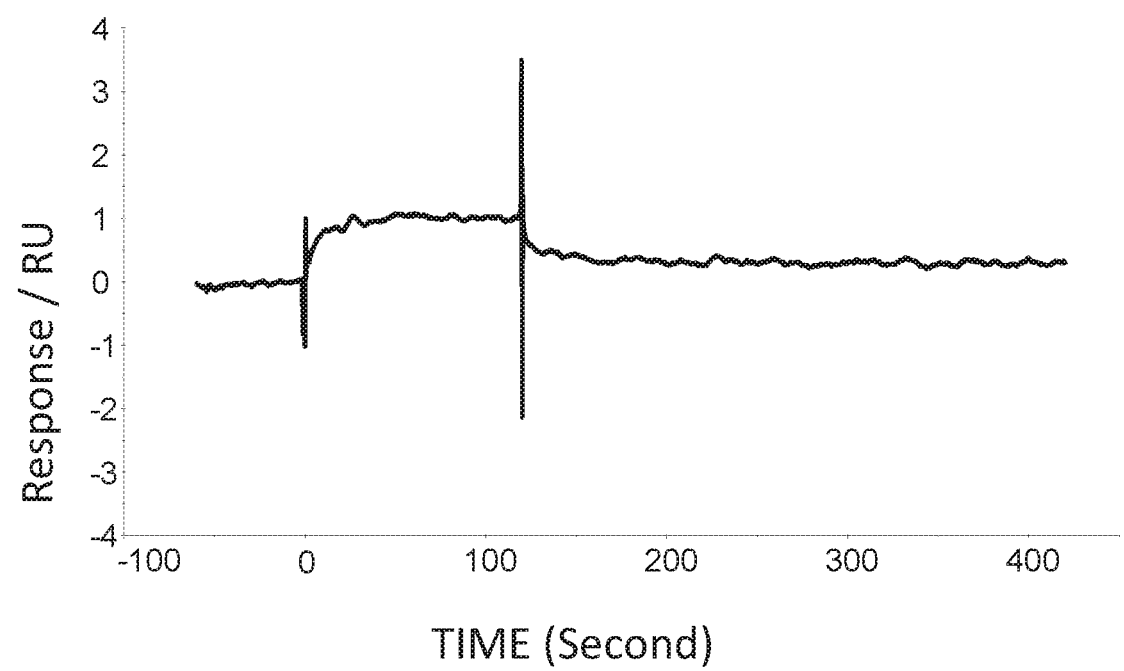

FIG. 8B is a graph showing the SPR evaluation result of the binding ability of the VHH antibody (concentration: 250 nM) including the amino acid sequence represented by SEQ ID NO: 43 to a norovirus.

Figure 8C:
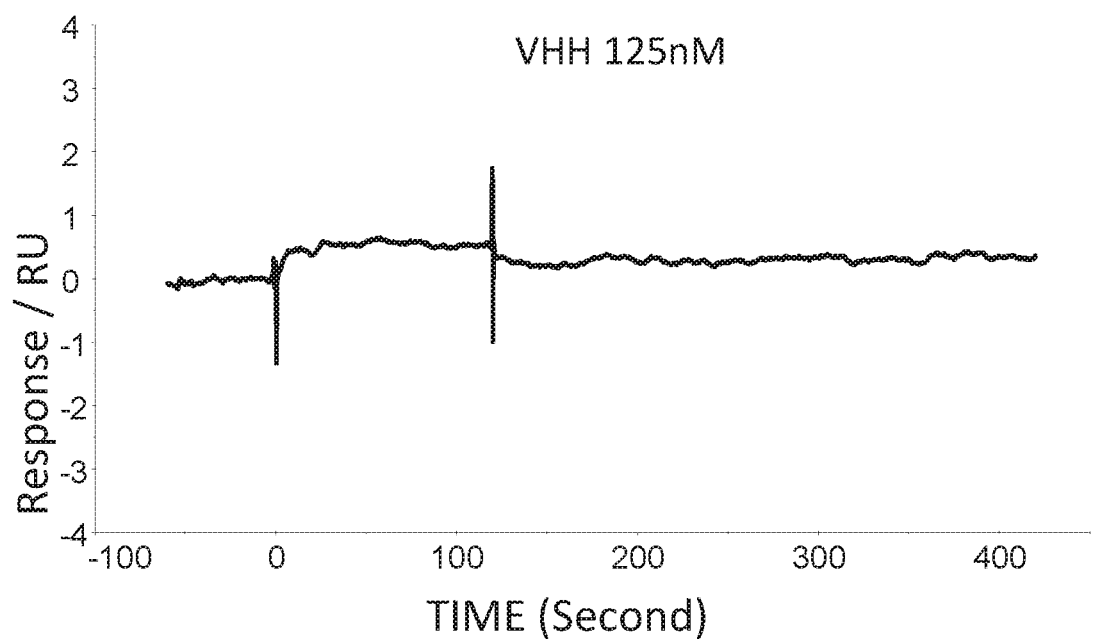

FIG. 8C is a graph showing the SPR evaluation result of the binding ability of the VHH antibody (concentration: 125 nM) including the amino acid sequence represented by SEQ ID NO: 43 to a norovirus.

Figure 8D:
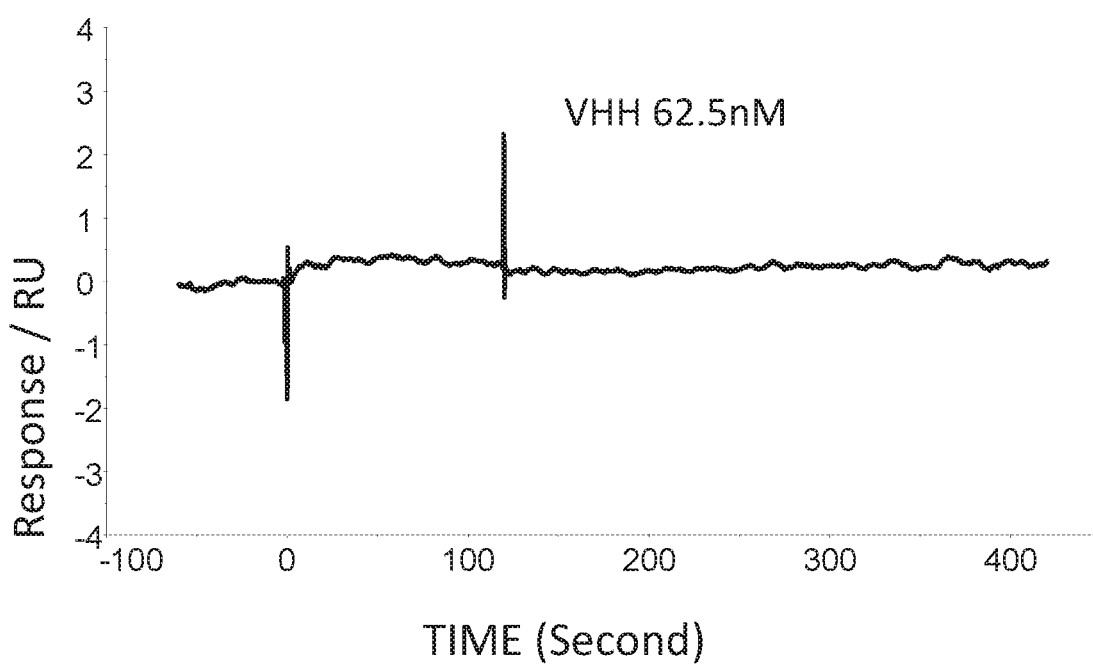

FIG. 8D is a graph showing the SPR evaluation result of the binding ability of the VHH antibody (concentration: 62.5 nM) including the amino acid sequence represented by SEQ ID NO: 43 to a norovirus.

Figure 8E:
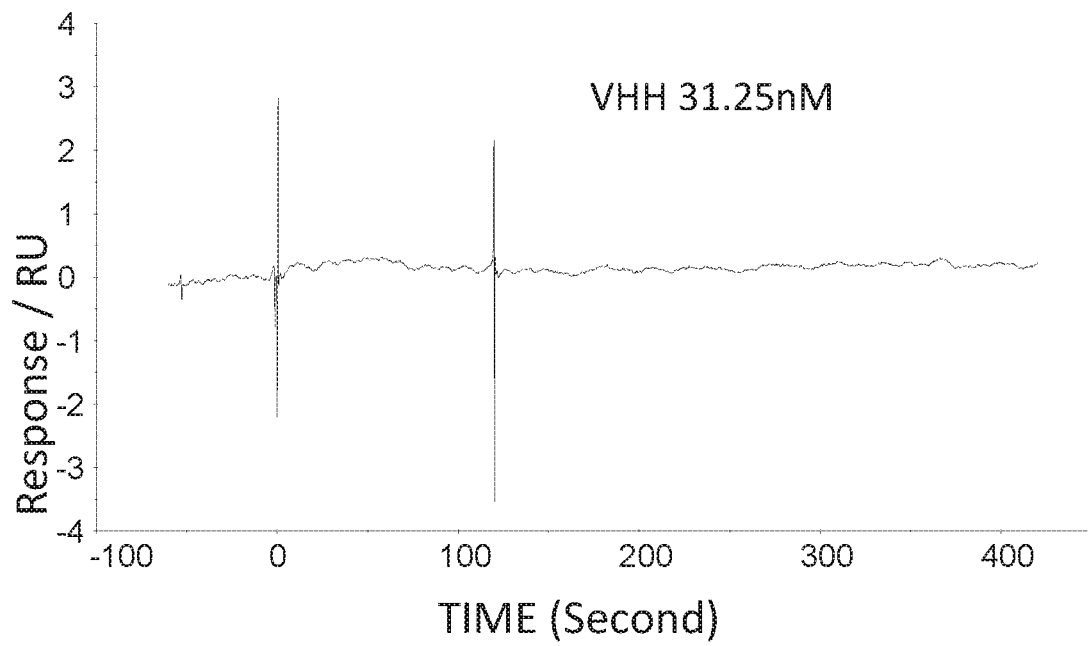

FIG. 8E is a graph showing the SPR evaluation result of the binding ability of the VHH antibody (concentration: 31.25 nM) including the amino acid sequence represented by SEQ ID NO: 43 to a norovirus.

Figure 8F:
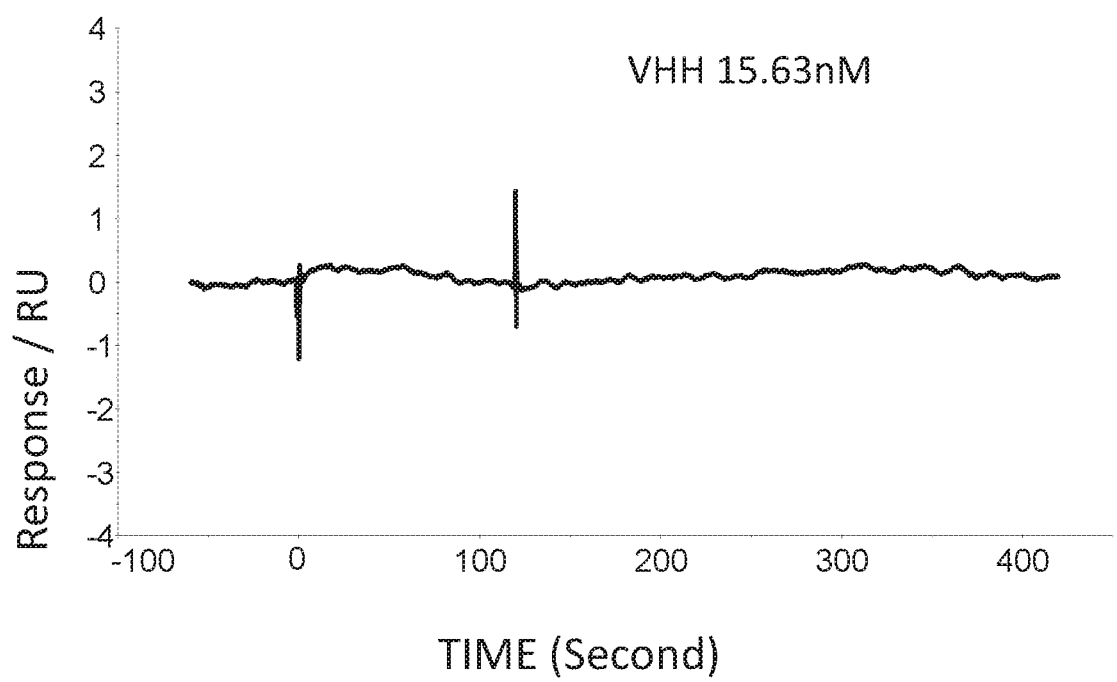

FIG. 8F is a graph showing the SPR evaluation result of the binding ability of the VHH antibody (concentration: 15.63 nM) including the amino acid sequence represented by SEQ ID NO: 43 to a norovirus.

Figure 8G:
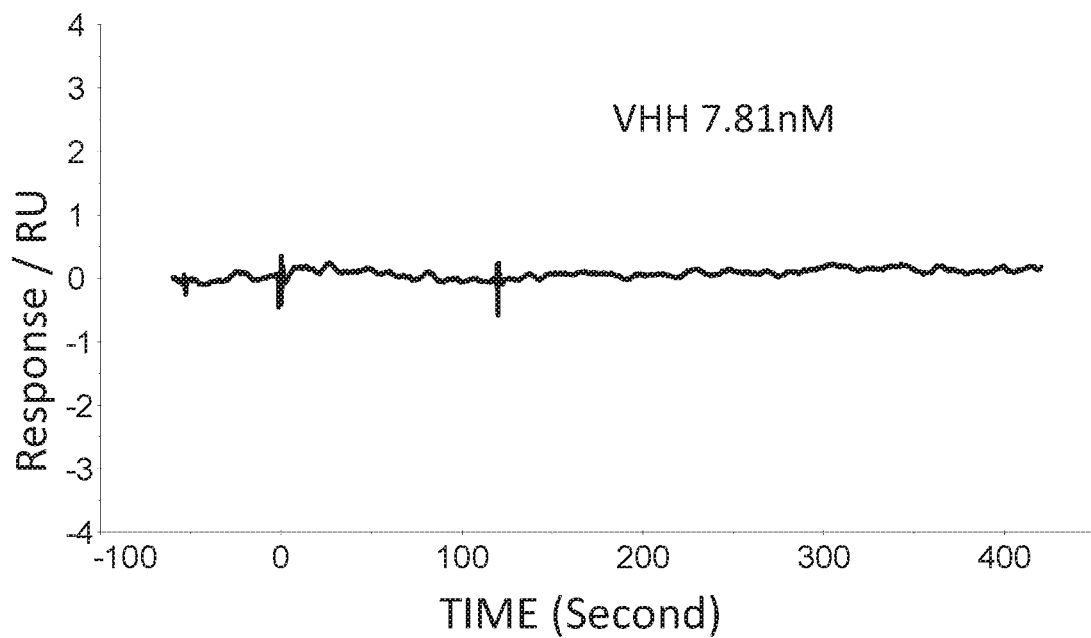

FIG. 8G is a graph showing the SPR evaluation result of the binding ability of the VHH antibody (concentration: 7.81 nM) including the amino acid sequence represented by SEQ ID NO: 43 to a norovirus.

Figure 8H:
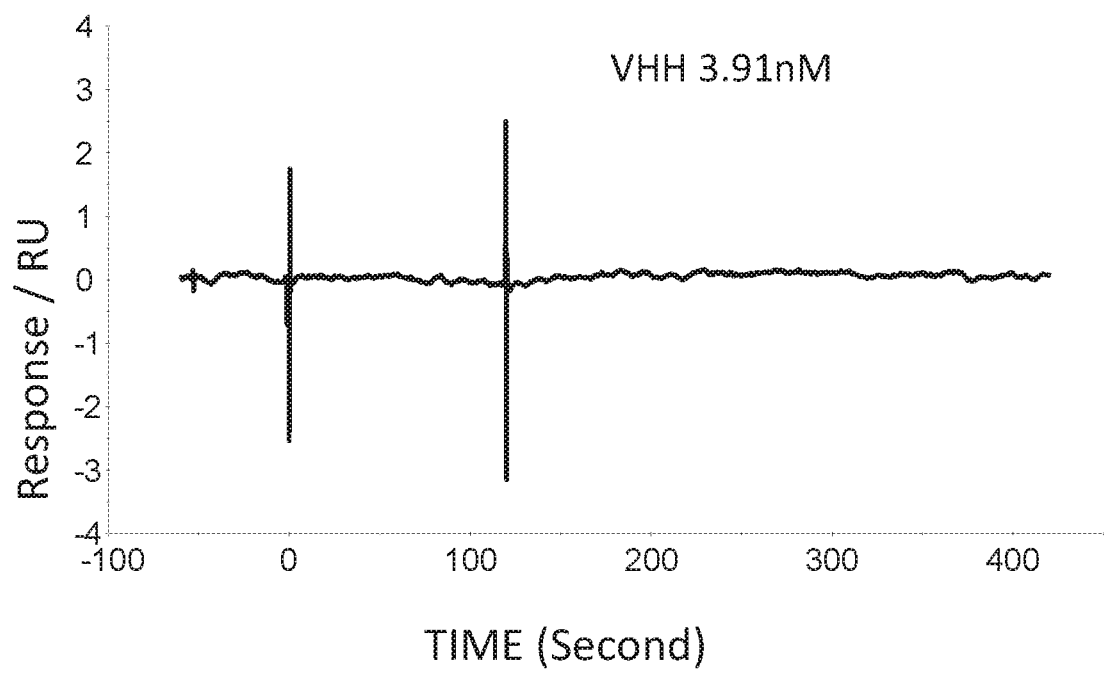

FIG. 8H is a graph showing the SPR evaluation result of the binding ability of the VHH antibody (concentration: 3.91 nM) including the amino acid sequence represented by SEQ ID NO: 43 to a norovirus.

FIG. 9 is a graph showing a SPR evaluation result of the binding ability of the immobilized VHH antibody including the amino acid sequence represented by SEQ ID NO: 38 to a noro antigen, the SPR evaluation result being provided by serially adding the noro antigens prepared so as to have a concentration of 1.6 nM, 8 nM, 40 nM, 200 nM, and 1000 nM.

FIG. 10 is a graph showing a SPR evaluation result of the binding ability of the immobilized VHH antibody including the amino acid sequence represented by SEQ ID NO: 39 to a noro antigen, the SPR evaluation result being provided by serially adding the noro antigens prepared so as to have a concentration of 1.6 nM, 8 nM, 40 nM, 200 nM, and 1000 nM.

FIG. 11 is a graph showing a SPR evaluation result of the binding ability of the immobilized VHH antibody including the amino acid sequence represented by SEQ ID NO: 40 to a noro antigen, the SPR evaluation result being provided by serially adding the noro antigens prepared so as to have a concentration of 1.6 nM, 8 nM, 40 nM, 200 nM, and 1000 nM.

FIG. 12 is a graph showing a SPR evaluation result of the binding ability of the immobilized VHH antibody including the amino acid sequence represented by SEQ ID NO: 41 to a noro antigen, the SPR evaluation result being provided by serially adding the noro antigens prepared so as to have a concentration of 1.6 nM, 8 nM, 40 nM, 200 nM, and 1000 nM.

FIG. 13 is a graph showing a SPR evaluation result of the binding ability of the immobilized VHH antibody including the amino acid sequence represented by SEQ ID NO: 42 to a noro antigen, the SPR evaluation result being provided by serially adding the noro antigens prepared so as to have a concentration of 1.6 nM, 8 nM, 40 nM, 200 nM, and 1000 nM.

FIG. 14 is a graph showing a SPR evaluation result of the binding ability of the immobilized VHH antibody including the amino acid sequence represented by SEQ ID NO: 43 to a noro antigen, the SPR evaluation result being provided by serially adding the noro antigens prepared so as to have a concentration of 1.6 nM, 8 nM, 40 nM, 200 nM, and 1000 nM.

DETAILED DESCRIPTION OF THE EMBODIMENT

The antibody according to the present invention is capable of binding to a norovirus. In particular, the antibody according to the present invention is capable of binding to a GII/4 norovirus. As disclosed in Patent Literature 1, an antibody capable of binding to a norovirus includes an amino acid sequence including, in an N- to C-direction, the following structural domains.

N-FR1-CDR1-FR2-CDR2-FR3-CDR3-FR4-C wherein

FR denotes a framework region amino acid sequence and CDR denotes a complementary determining region amino acid sequence.

In the present invention, the CDR1 includes any one of amino acid sequences represented by SEQ ID NO: 1-SEQ ID NO: 6.

In the present invention, the CDR2 includes any one of amino acid sequences represented by SEQ ID NO: 7-SEQ ID NO: 12.

In the present invention, the CDR3 includes any one of amino acid sequences represented by SEQ ID NO: 13-SEQ ID NO: 17.

Desirably, the CDR1, the CDR2, and the CDR3 are represented by SEQ ID NO: 1-SEQ ID NO: 6, SEQ ID NO: 7-SEQ ID NO: 12, and SEQ ID NO: 13-SEQ ID NO: 17, respectively. In this case, more desirably, the FR1, the FR2, the FR3, and the FR4 consist of amino acid sequences represented by SEQ ID NO: 18-SEQ ID NO: 23, SEQ ID NO: 24-SEQ ID NO: 28, SEQ ID NO: 29-SEQ ID NO: 34, and SEQ ID NO: 35-SEQ ID NO: 37, respectively. In other words, it is desirable that the antibody according to the present invention includes any one of the amino acid sequences represented by SEQ ID NO: 38-SEQ ID NO: 43.

The antibody including any one of the amino acid sequences represented by SEQ ID NO: 38-SEQ ID NO: 43 is capable of binding the norovirus, especially, the GII/4 norovirus.

Note that "include" includes "consist of" and "essentially consist of" in the present specification.

The antibody according to the present invention can be employed in a detection device or in a detection method for detecting the norovirus. In this case, the antibody according to the present invention may be used in a state of a composite bound to another material, for example, in a state of a composite in which the antibody according to the present invention has been bound to at least one selected from the group consisting of a solid phase support and a labeled substance.

As long as the solid phase support is a support insoluble in a solvent used for a reaction system of an antigen-antibody reaction, a shape and a material of the solid phase support is not limited. An example of the shape of the solid phase support is a plate, a bead, a disk, a tube, a filter, and a film. An example of a material of the solid phase support is a polymer such as polyethylene terephthalate, cellulose acetate, polycarbonate, polystyrene, or polymethylmethacrylate, a metal such as gold, silver, or aluminum, or glass. A known method such as a physical adsorption method, a covalent binding method, an ion bonding method, or a cross-linking method is employed as a method for binding the antibody to the solid phase support.

For example, a labeled substance such as a fluorescent substance, a luminescent substance, a dye, an enzyme, or a radioactive substance is used. A known method such as a physical adsorption method, a covalent binding method, an ion bonding method, or a cross-linking method is employed as a method for binding the antibody to the labeled substance.

In the detection method in which the antibody according to the present invention is used, the composite including the antibody is brought into contact with an analyte. Then, detected is a change of a physical amount based on an antigen-antibody reaction of the norovirus contained in the analyte and the antibody included in the composite. An example of the physical amount is luminescence intensity, chromaticity, light transmission, turbidness, absorbance, or radiation dose. A known method such as an enzyme immunoassay method, an immunochromatography method, a latex agglutination method, a radioimmunoassay method, a fluorescence immunoassay method, or a surface plasmon resonance spectroscopy method is employed as an example of the detection method.

The detection device in which the antibody according to the present invention is employed includes a detector for detecting any one of the physical amount which is changed on the basis of the antigen-antibody reaction. The detector is composed of a known device such as a photometer, a spectroscope, or a dosimeter.

The antibody may be used not only as a composite bound to another material but also as a composition including the antibody according to the present invention or as a kit including the antibody according to the present invention.

EXAMPLES

Inventive Example 1

VHH antibodies (i.e., a variable domain of a heavy chain of a heavy chain antibody) were prepared in accordance with the following procedures as a peptide capable of binding to a protein which exists on a surface of a GII/4 norovirus.

(Immunization of Alpaca and Acquirement of Mononuclear)

In order to form a VHH antibody gene library, an antigen derived from the GII/4 norovirus (NSW-2012) was prepared. In other words, a p-domain protein of the GII/4 norovirus (NSW-2012), which is a capsid protein existing on the surface of the norovirus, was converted into its recombinant. An alpaca was immunized using the recombinant p-domain protein as the antigen of the norovirus (SEQ ID NO: 44). Hereinafter, the antigen of the norovirus is referred to as "noro antigen". The noro antigen was prepared with an adjuvant before the immunization of the alpaca.

The sequence of the noro antigen (SEQ ID NO: 44, which is a recombinant of the p-domain protein of the GII/4 norovirus (NSW-2012)) used in the inventive example 1 was shown below.

```
                                         (SEQ ID NO: 44)
MKMASNDANPSDGSTANLVPEVNNEVMALEPVVGAAIAAPVAGQQNVIDP

WIRNNFVQAPGGEFTVSPRNAPGEILWSAPLGPDLNPYLSHLARMYNGYA

GGFEVQVILAGNAFTAGKIIFAAVPPNFPTEGLSPSQVTMFPHIIVDVRQ

LEPVLTPLPDVRNNFYHYNQSNDPTIKLIAMLYTPLRANNAGDDVFTVSC

RVLTRPSPDFDFIFLVPPTVESRTKPFSVPVLTVEEMTNSRFPIPLEKLF

TGPSSAFVVQPQNGRCTTDGVLLGTTQLSPVNICTFRGDVTHITGSRNYT

MNLASQNWNSYDPTEEIPAPLGTPDFVGKIQGVLTQTTRTDGSTRGHKAT

VYTFSADFSPKLGRVQFATDTDNDFETNQNTKFTPVGVIQDGGTTHRNEP

QQWVLPSYSGRNTHNVHLAPAVAPTFPGEQLLFFRSTMPGCSGYPNMDLD

CLLPQEWVQYFYQEAAPAQSDVALLRFVNPDTGRVLFECKLHKSGYVTVA

HTGQHDLVIPPNGYFRFDSWVNQFYTLAPMGNGTGRRRAL
```

Specifically, the noro antigen having a concentration of 100 micrograms/milliliter was administered to the alpaca. After one week, the noro antigen having the same concentration was administered to the alpaca, again. In this way, the alpaca was immunized with the noro antigen five times over five weeks. After another week, blood of the alpaca was extracted. Then, mononuclear cells were acquired from the blood as below.

A blood cell separation solution (available from COSMO BIO Co., Ltd., trade name: Lymphoprep) was added to a lymphocyte separation tube (available from Greiner Bio-One Co., Ltd., trade name: Leucosep). Then, the solution was subjected to centrifugation at 1,000×g at a temperature of 20 degrees Celsius for one minute.

The blood extracted from the alpaca was treated with heparin. Then, an equivalent amount of phosphate buffered saline (hereinafter, referred to as "PBS") was added to the thus-treated blood to provide a sample solution. Then, the sample solution was added to the lymphocyte separation tube containing the blood cell separation solution.

The lymphocyte separation tube was subjected to centrifugation at 800×g at a temperature of 20 degrees Celsius for thirty minutes.

A fraction containing mononuclear cells was collected. Three times its volume of PBS was added. The fraction was subjected to centrifugation at 300×g at a temperature of 20 degrees Celsius for five minutes. The precipitate was suspended with PBS gently. After the suspending, 10 microliters of the suspension was separated in order for the count of the number of cells. The remaining suspension was subjected to centrifugation at 300×g at a temperature of 20 degrees Celsius for five minutes.

An RNA storage solution (trade name: RNAlater) having a volume of 2 milliliters was added to the precipitate. Then, the solution was suspended gently. The suspension was injected into two tubes each having a volume of 1.5 milliliters. Each tube contained 1 milliliter of the suspension. The tube was stored at a temperature of −20 degrees Celsius. The suspension (5 microliters) separated for the count of the number of cells was mixed with a Turk's solution (15 microliters), and the number of the mononuclear cells was counted with a counting chamber.

(Formation of cDNA Gene Library of VHH Antibody)

Then, a total RNA was extracted from the mononuclear cells, and a cDNA gene library of the VHH antibody was formed in accordance with the following procedure. In the following procedure, RNase-free-grade reagents and instruments were used.

A total RNA isolation reagent (trade name: TRTzol Regent, 1 milliliter) was added to the mononuclear cell fraction. The reagent was mixed gently with the fraction, and left at rest at room temperature for five minutes. Chloroform (200 microliters) was added to the reagent, and the reagent was shaken strongly for fifteen seconds. The reagent was left at rest at room temperature for two-three minutes. The reagent was subjected to centrifugation at 12, 000×g or less at a temperature of 4 degrees Celsius for 15 minutes.

The supernatant was moved to a new tube. RNase-free water and chloroform (200 microliters, each) were added to the tube. In addition, 500 milliliters of isopropanol was added to the tube. The liquid contained in the tube was stirred with a vortex mixer. The liquid was left at rest at room temperature for ten minutes. Then, the liquid was subjected to centrifugation at 12,000×g or less at a temperature of 4 degrees Celsius for fifteen minutes. The supernatant was removed, and the precipitate was rinsed with one milliliter of 75% ethanol. This solution was subjected to centrifugation at 7,500×g or less at a temperature of four degrees Celsius for five minutes. The solution was dried to obtain total RNA. The obtained total RNA was dissolved in RNase-free water.

In order to obtain cDNA from the total RNA, a kit including a reverse transcriptase was employed. The kit was available from Takara Bio Inc., as a trade name of PrimeScript II $1^{st}$ strand cDNA Synthesis Kit. The Random 6 mer and Oligo dT primer included in the kit were used as primers. The cDNA was obtained in accordance with the standard protocol attached to the kit.

The gene of the VHH antibody included in the alpaca was obtained from the cDNA by a PCR method. An enzyme for PCR was available from Takara Bio Inc., as a trade name of Ex-taq.

The following reagents were mixed to obtain a mixture solution.

10× buffer 5 microliters
dNTPs 4 microliters
Primer F 2 microliters
Primer R 2 microliters
cDNA template 1 microliter
Ex-taq 0.25 microliters The mixture solution was subjected to the following PCR method.

First, the mixture solution was heated at a temperature of 95 degrees Celsius for two minutes.

Then, the temperature of the mixture solution was varied in accordance with the following cycle.

Ninety six degrees Celsius for thirty seconds,
Fifty two degrees Celsius for thirty seconds, and
Sixty eight degrees Celsius for forty seconds
This cycle was repeated thirty times.

Finally, the mixture solution was heated at a temperature of sixty eight degrees Celsius for four minutes and stored at a temperature of four degrees Celsius.

The following primers were used in the present PCR method.

Primer 1:
(SEQ ID NO: 45)
5'-GGTGGTCCTGGCTGC-3'

Primer 2:
(SEQ ID NO: 46)
5'-ctgctcctcgcGGCCCAGCCGGCCatggcTSAGKTGCAGCTCGTGGAGTC-3'

Primer 3:
(SEQ ID NO: 47)
5'-TGGGGTCTTCGCTGTGGTGCG-3'

Primer 4:
(SEQ ID NO: 48)
5'-TTGTGGTTTTGGTGTCTTGGG-3'

Primer 5:
(SEQ ID NO: 49)
5'-tttgCtctGCGGCCGCagaGGCCgTGGGGTCTTCGCTGTGGTGCG-3'

Primer 6:
(SEQ ID NO: 50)
5'-tttgCtctGCGGCCGCagaGGCCgaTTGTGGTTTTGGTGTCTTGGG-3'

(Reference literature: Biomed Environ Sci., 2012; 27(2): 118-121)

Three PCR assays were conducted.

In the first PCR assay, a primer set A composed of the cDNA, Primer 1 and Primer 3 and a primer set B composed of the cDNA, Primer 1 and Primer 4 were used.

In the second PCR assay, a primer set C composed of the gene amplified with the primer set A, Primer 2, and Primer 3, and a primer set D composed of the gene amplified with the primer set B, Primer 2, and Primer 4 were used.

In the third PCR assay, a primer set E composed of the gene amplified with the primer set C, Primer 2, and Primer 5, and a primer set F composed of the gene amplified with the primer set D, Primer 2, and Primer 6 were used.

In this way, the gene library of the VHH antibody was formed. In other words, the gene library of the VHH antibody included the genes amplified with the primer sets E and F.

(Formation of Phage Library)

Next, a phage library was formed from the gene library of the VHH antibody in accordance of the following procedures.

Figure 1A:
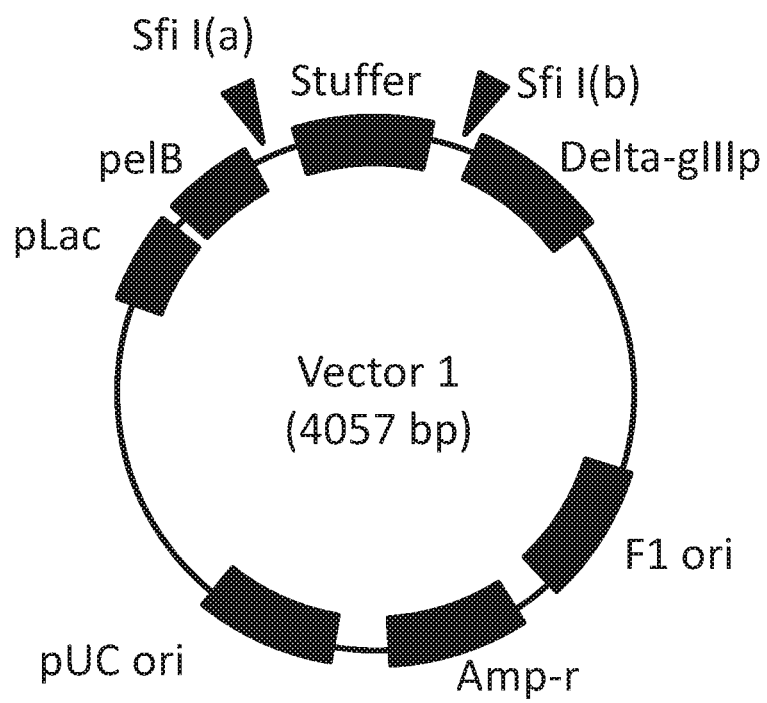
FIG. 1A is a map of a vector used to ligate various genes included in a gene library of a VHH antibody.
Figure 1B:
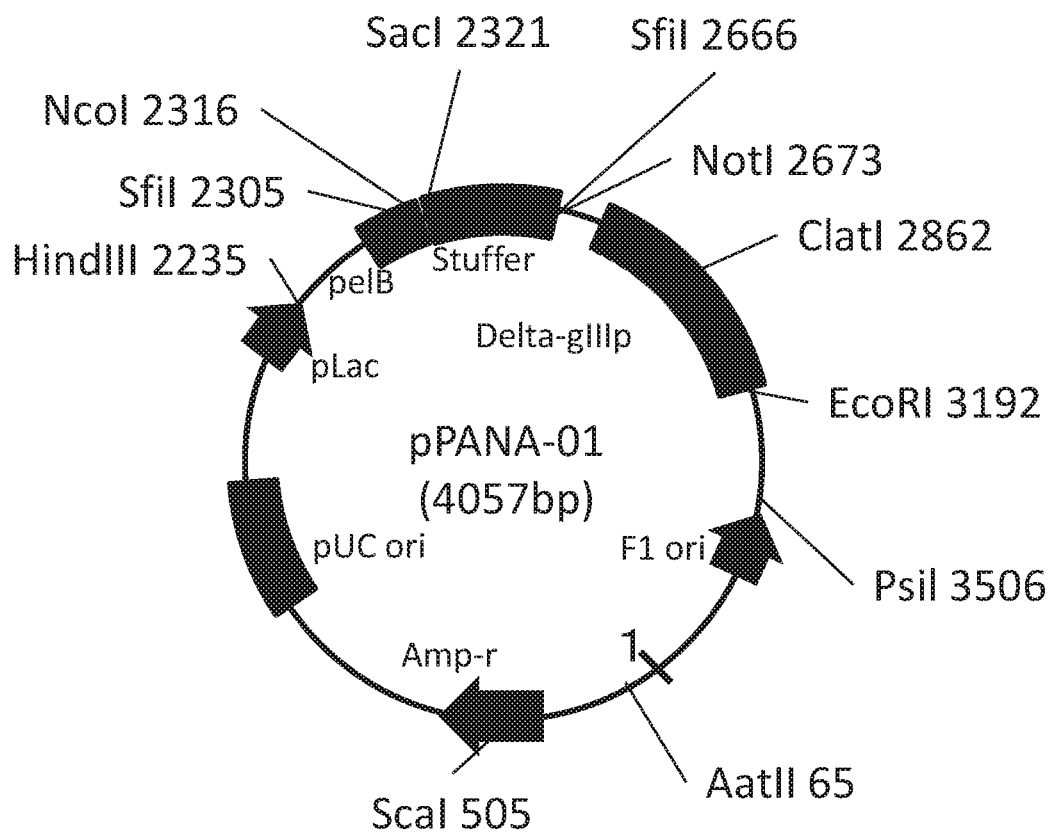
FIG. 1B shows the detail of the vector map shown in FIG. 1A.

A plasmid Vector 1 (4057 bp, see FIG. 1A) derived from a commercially available plasmid pUC119 (for example, available from Takara Bio Inc.) was treated with a restriction enzyme SfiI. The restriction enzyme site SfiI(a) consists of the gene sequence represented by GGCCCAGCCGGCC (SEQ ID NO: 51). The restriction enzyme site SfiI(b) consists of the gene sequence represented by GGCCTCTGCGGCC (SEQ ID NO: 52). FIG. 1B shows a detailed vector map of the plasmid Vector 1.

The plasmid Vector 1 consists of the following gene sequence.

(SEQ ID NO: 77)
gacgaaagggcctcgtgatacgcctatttttataggttaatgtcatgata ataatggtttcttagacgtcaggtggcacttttcggggaaatgtgcgcg gaacccctatttgtttattttctaaatacattcaaatatgtatccgctc atgagacaataaccctgataaatgcttcaataatattgaaaaaggaagag tatgagtattcaacatttccgtgtcgcccttattcccttttttgcggcat -continued

```
tttgccttcctgttttgctcacccagaaacgctggtgaaagtaaaagat
gctgaagatcagttgggtgcacgagtgggttacatcgaactggatctcaa
cagcggtaagatccttgagagttttcgccccgaagaacgttttccaatga
tgagcacttttaaagttctgctatgtggcgcggtattatcccgtattgac
gccgggcaagagcaactcggtcgccgcatacactattctcagaatgactt
ggttgagtactcaccagtcacagaaaagcatcttacggatggcatgacag
taagagaattatgcagtgctgccataaccatgagtgataacactgcggcc
aacttacttctgacaacgatcggaggaccgaaggagctaaccgcttttt
gcacaacatggggatcatgtaactcgccttgatcgttgggaaccggagc
tgaatgaagccataccaaacgacgagcgtgacaccacgatgcctgtagca
atggcaacaacgttgcgcaaactattaactggcgaactacttactctagc
ttcccggcaacaattaatagactggatggaggcggataaagttgcaggac
cacttctgcgctcggccttccggctggctggtttattgctgataaatct
ggagccggtgagcgtgggtctcgcggtatcattgcagcactggggccaga
tggtaagccctcccgtatcgtagttatctacacgacggggagtcaggcaa
ctatggatgaacgaaatagacagatcgctgagataggtgcctcactgatt
aagcattggtaactgtcagaccaagtttactcatatactttagattga
tttaaaacttcattttaatttaaaaggatctaggtgaagatcctttttg
ataatctcatgaccaaaatcccttaacgtgagttttcgttccactgagcg
tcagacccgtagaaaagatcaaaggatcttcttgagatcctttttttct
gcgcgtaatctgctgcttgcaaacaaaaaaaccaccgctaccagcggtgg
tttgtttgccggatcaagagctaccaactctttttccgaaggtaactggc
ttcagcagagcgcagataccaaatactgtcctctagtgtagccgtagtt
aggccaccacttcaagaactctgtagcaccgcctacatacctcgctctgc
taatcctgttaccagtggctgctgccagtggcgataagtcgtgtcttacc
gggttggactcaagacgatagttaccggataaggcgcagcggtcgggctg
aacgggggttcgtgcacacagcccagcttggagcgaacgacctacaccg
aactgagatacctacagcgtgagctatgagaaagcgccacgcttcccgaa
gggagaaaggcggacaggtatccggtaagcggcagggtcggaacaggaga
gcgcacgagggagcttccaggggggaaacgcctggtatctttatagtcctg
tcgggtttcgccacctctgacttgagcgtcgatttttgtgatgctcgtca
gggggcggagcctatggaaaaacgccagcaacgcggcctttttacggtt
cctggccttttgctggccttttgctcacatgttctttcctgcgttatccc
ctgattctgtggataaccgtattaccgcctttgagtgagctgataccgct
cgccgcagccgaacgaccgagcgcagcgagtcagtgagcgaggaagcgga
agagcgcccaatacgcaaaccgcctctccccgcgcgttggccgattcatt
aatgcagctggcacgacaggtttcccgactggaaagcgggcagtgagcgc
aacgcaattaatgtgagttagctcactcattaggcaccccaggctttaca
ctttatgcttccggctcgtatgttgtgtggaattgtgagcggataacaat
ttcacacaggaaacagctatgaccatgattacgccAAGCTTCGAAGGAGA
CAGTCATAatgaaatacctgctgccgaccgctgctgctggtctgctgctc
```

```
ctcgcGGCCCAGCCGGCCatggagcTCAAGATGACACAGACTACATCCTC
CCTGTCAGCCTCTCTGGGAGACAGAGTCACCATCAGTTGCAGGGCAAGTC
AGGACATTAGCgATTATTTAAACTGGTATCAGCAGAAACCAGATGGAACT
GTTAAACTCCTGATCTATTACACATCAAGTTTACACTCAGGAGTCCCATC
AAGGTTCAGTGGCGGTGGGTCTGGAACAGATTATTCTCTCACCATTAGCA
ACCTGGAGCAAGAAGATATrGCCACTTACTTTTGCCAACAGGGTAATACG
CTTCCGTGGACGTTTGGTGGAGGCACCAAGCTGGAAATCAAACGGGCTGA
TGCTGCACCAACTgtaGGCCtctGCGGCCGCagaGcaaaaactcatctca
gaagaggatctgaatggggccgcaTAGggttccggtgattttgattatga
aaagatggcaaacgctaataaggggctatgaccgaaaatgccgatgaaa
acgcgctacagtctgacgctaaaggcaaacttgattctgtcgctactgat
tacggtgctgctatcgatggtttcattggtgacgtttccggccttgctaa
tggtaatggtgctactggtgattttgctggctctaattcccaaatggctc
aagtcggtgacggtgataattcacctttaatgaataatttccgtcaatat
ttaccttccctccctcaatcggttgaatgtcgccttttgtctttagcgc
tggtaaaccatatgaattttctattgattgtgacaaaataaacttattcc
gtggtgtctttgcgtttcttttatatgttgccacctttatgtatgtattt
tctacgtttgctaacatactgcgtaataaggagtctTAATAAgaattcac
tggccgtcgttttacaacgtcgtgactgggaaaaccctggcgttacccaa
cttaatcgccttgcagcacatccccctttcgccagctggcgtaatagcga
agaggcccgcaccgatcgcccttcccaacagttgcgcagcctgaatggcg
aatggcgcctgatgcggtattttctccttacgcatctgtgcggtatttca
caccgCATATGaAAATTGTAAgcgttaatattttgttaaaattcgcgtta
aattttgttaaatcagctcattttttaaccaataggccgaaatcggcaa
aatcccttataaatcaaaagaatagaccgagatagggttgagtgttgttc
cagtttggaacaagagtccactattaaagaacgtggactccaacgtcaaa
gggcgaaaaaccgtctatcagggcgatggcccactacgtgaaccatcacc
ctaatcaagttttttggggtcgaggtgccgtaaagcactaaatcggaacc
ctaaagggagccccgatttagagcttgacggggaaagccggcgaacgtg
gcgagaaaggaagggaagaaagcgaaaggagcgggcgctagggcgctggc
aagtgtagcggtcacgctgcgcgtaaccaccacaccgcgcgcttaatg
cgccgctacaGGGCGCGTcccatATGgtgcactctcagtacaatctgctc
tgatgccgcatagttaagccagccccgacacccgccaacacccgctgacg
cgccctgacgggcttgtctgctcccggcatccgcttacagacaagctgtg
accgtctccgggagctgcatgtgtcagaggttttcaccgtcatcaccgaa
acgcgcga
```

Similarly, the gene library of the VHH antibody was treated with the restriction enzyme SfiI. In this way, VHH antibody gene fragments were obtained.

The thus-treated plasmid Vector 1 was mixed with the VHH antibody gene fragments at a ratio of 1:2. An enzyme (available from Toyobo Co. Ltd., trade name: Ligation High ver. 2) was injected into the mixture solution. The mixture solution was left at rest at a temperature of 16 degrees Celsius for two hours. In this way, each of the VHH antibody gene fragments was ligated into the plasmid Vector 1.

*Coli* bacteria (available from Takara Bio Inc., trade name: HST02) were transfected with the thus-ligated plasmid Vector 1.

Then, the *coli* bacteria were incubated for fifteen hours on a 2YT plate culture medium containing ampicillin at a concentration of 100 micrograms/milliliter. In this way, obtained was a library of phages each of which displays a protein obtained from the gene fragment included in the gene library of the VHH antibody.

After the incubation, a concentration of the library was calculated by counting the number of single colonies formed on the 2YT plate culture medium. As a result, the library of the phages had a concentration of 5E+7/milliliter.

(Biopanning)

VHH antibodies capable of specifically binding to the noro antigen (i.e., the recombinant of the p-domain protein of the GII/4 norovirus (NSW-2012), the recombinant being represented by SEQ ID NO: 44) were obtained from the phage library in accordance with the following procedures.

In order to extract the clones each capable of binding to the antigen from among the phages which expressed the VHH antibody, biopanning was conducted twice.

*Coli* bacteria (HST02) to which the VHH antibody gene fragment included in the gene library of the VHH antibody had been introduced were incubated at a temperature of 30 degrees Celsius in the 2YT AG culture medium containing 100 micrograms/milliliter of ampicillin and 1% glucose until a value $OD_{600}$ indicating absorbance reached 1.0. The 2YT AG culture medium had a volume of 100 milliliters. In this way, the *coli* bacteria were proliferated.

Helper phages (available from Invitrogen company, trade name: M13K07) were added to the *coli* bacteria culture medium in such a manner that the multiplicity of infection (hereinafter, referred to as "MOI") was approximately twenty.

Then, the culture medium was warmed for about thirty minutes at a temperature of 37 degrees Celsius. Then, the culture medium was subjected to centrifugation at a rotation speed of 4000 rpm for ten minutes to collect the *coli* bacteria. The *coli* bacteria were incubated overnight at a temperature of 30 degrees Celsius in a 2YTAK culture medium containing 100 micrograms/milliliter of ampicillin and 50 micrograms/milliliter of kanamycin, while subjected to centrifugation at 213 rpm. The 2YTAK culture medium had a volume of 100 milliliters.

The incubation liquid (100 milliliters) containing the thus-incubated *coli* bacteria was injected into two centrifugation tubes (volume: 50 milliliters, each). The two centrifugation tubes were subjected to centrifugation for ten minutes at a rotation speed of 4,000 rpm. Then, the supernatants (20 milliliters, each) were collected.

The supernatants (40 milliliters) were added to a 20% polyethylene glycol solution (10 milliliters) containing NaCl (2.5 M). Then, the mixture solution was inverted and mixed. Subsequently, the mixture solution was cooled on ice for approximately one hour. The mixture was subjected to centrifugation for ten minutes at a rotation speed of 4, 000 rpm. Then, the supernatant was removed. PBS containing 10% glycerol was injected toward the precipitate. Finally, the precipitate was loosened and dissolved. In this way, a library of phages each of which displays the VHH antibody was obtained.

(Screening of VHH Antibody Capable of Specifically Binding to Noro Antigen)

(A) Immobilization of Noro Antigen

The norovirus was mixed with PBS to prepare a norovirus solution. The concentration of norovirus was 2 micrograms/milliliter. The norovirus solution (2 milliliters) was injected into an immunotube (available from NUNC Co. Ltd.). The norovirus solution was left at rest overnight in the immunotube. In this way, norovirus was immobilized in the immunotube.

Then, the inside of the immunotube was washed three times with PBS.

The inside of the immunotube was filled with PBS which contained 3% skim milk (available from Wako Pure Chemical Industries, Ltd.). In this way, norovirus was blocked as an antigen in the immunotube.

The immunotube was left at rest at room temperature for one hour. Subsequently, the inside of the immunotube was washed three times with PBS.

(B) Panning

The library of the phages each of which displays the VHH antibody (concentration: approximately 5E+11/milliliter) was mixed with 3 milliliters of PBS containing 3% skim milk to prepare a mixture solution. The mixture solution was injected into the immunotube in which the noro antigen was immobilized.

The immunotube was provided with a lid formed of Parafilm. Then, the immunotube was rotated upside down in a rotator for ten minutes.

The immunotube was left at rest at room temperature for one hour.

The inside of the immunotube was washed ten times with PBS containing 0.05% Tween 20. Hereinafter, such PBS is referred to as "PBST".

The inside of the immunotube was filled with PBST. Subsequently, the immunotube was left at rest for ten minutes. Then, the inside of the immunotube was washed ten times with PBST.

In order to extract phages each of which displays the VHH antibody bound to the noro antigen, 100 mM trimethylamine solution (1 milliliter) was injected into the immunotube.

The immunotube was provided with a lid formed of Parafilm. Then, the immunotube was rotated upside down in a rotator for ten minutes.

In order to neutralize the solution, the solution was moved to a tube containing 1 mL of 0.5 M Tris/HCl (pH: 6.8). Again, the extraction of the phage was repeated using a 100 mM trimethylamine solution (1 milliliter). In this way, 3 mL of an extraction liquid was obtained.

The extraction liquid (1 mL) was mixed with 9 mL of *coli* bacteria HST02. The mixture solution was left at rest for one hour at a temperature of 30 degrees Celsius.

In order to count the number of colonies, 10 microliters of the mixture solution containing the *coli* bacteria HST02 was distributed onto a small plate containing a 2TYA culture medium (10 milliliters/plate).

The rest of the mixture solution was subjected to centrifugation. The supernatant was removed, and the precipitate was distributed onto a large plate containing a 2TYA culture medium (40 milliliters/plate). These two plates were left at rest overnight at a temperature of 30 degrees Celsius. In this way, first panning was conducted.

Second panning was conducted identically to the procedure of the first panning. In other words, the panning was repeated. In this way, the monoclonal phages on which the VHH antibody was displayed were purified.

After the second panning, a colony of the *coli* bacteria was picked up with a toothpick. The picked-up one colony was put onto one well of 96-flat-bottom plate. This was repeated. One well contained 200 microliters of a 2YTAG culture medium.

The solutions contained in the wells were stirred at a rotation speed of 213 rpm at a temperature of 30 degrees Celsius.

The solution (50 microliters) containing grown *coli* bacteria was collected. The collected solution was mixed with 50 microliters of a 2YTA culture medium contained in a plate. The 2YTA culture medium contained helper phages such that the multiplicity of infection (i.e., MOI) was set to be 20. The solution was left at rest at a temperature of 37 degrees Celsius for forty minutes.

The plate containing the 2YTA culture medium was subjected to centrifugation at 1,800 rpm for twenty minutes. The supernatant was removed. The precipitate contained the *coli* bacteria. The precipitate was mixed with 200 microliters of a 2YTAK culture medium. The mixture solution was left at rest overnight at a temperature of 30 degrees Celsius.

The mixture solution was subjected to centrifugation at 1,800 rpm for twenty minutes. The supernatant containing the *coli* bacteria was collected.

(C) Qualitative Evaluation of Phage-Displayed VHH Antibody and Antigen by ELISA

A solution containing the noro antigen (i.e., the recombinant of the p-domain protein of the GII/4 norovirus (NSW-2012), the recombinant being represented by SEQ ID NO: 44) having a concentration of 2 micrograms/milliliter was injected as an antigen into each of the wells of a 96-well plate (available from Thermo Fisher Scientific K.K., trade name: maxisorp). The volume of the solution containing the noro antigen in each well was 50 microliters. The 96-well plate was left at rest overnight at a temperature of 4 degrees Celsius. In this way, the noro antigen was immobilized in each well.

Each of the wells was washed with PBS three times. Then, PBS containing 3% skim milk (available from Wako Pure Chemical Industries, Ltd.) was injected into each well (200 microliters/well). The 96-well plate was left at rest at room temperature for one hour. In this way, the noro antigen was blocked in each well. Subsequently, each well was washed three times with PBS.

The monoclonal phages each of which displays the VHH antibody were injected into each well (50 microliters/well). Then, the 96-well plate was left at rest for one hour. In this way, the phages reacted with the noro antigen.

Each well was washed three times with PBST. Then, an anti-M13 antibody (available from ABCAM company, trade name: ab50370, 10,000-fold dilution) was injected into each well (50 microliters/well). Then, each well was washed three times with PBST.

A color-producing agent (available from Thermo Scientific, trade name: 1-step ultra TMB-ELISA) was injected into each well (50 microliters/well). The 96-well plate was left at rest for two minutes to cause the color-producing agent to react with the antibody.

A sulfuric acid aqueous solution (normal, i.e., 1 N) was injected into each well at a concentration of 50 microliters/well to cease the reaction.

The absorbance of the solution at a wavelength of 450 nanometers was measured.

Six wells each having good absorbance measurement result were selected. The DNA sequences included in the phages contained in the selected six wells were analyzed by Greiner Company. The analysis results of the DNA sequences will be described below. The following six DNA sequences were found.

```
                                        (SEQ ID NO: 53)
caggtgcagctcgtggagtctggggggaggtgtggtgcagactgggggtc tctgagactttcctgtgcagcctctggaagtactttcagtatcggtgcca tgggctggtaccgccaggcgccagggaagcagcgcgagttggtcgccact gttaatcgggcttctcggacaatctatgcagactccgtgagggccgatt caccatctccagagacaatgccaagaatttggtgtatctgcaaatgaaca acctgaaacctgaggacacagccgtctattattgtaatgtaatagcgacc agcgcgtcggggcgcggggtcacgtcgacttcgtggggccaggggtctca ggtcaccgtctcctcggaacccaagacaccaaaaccacaatcggcctctg cggcc
                                        (SEQ ID NO: 54)
cagttgcagctcgtggagtctggggagggcttggtgcaggctgggggtc tctgagactctcctgtgtagcctctggattcccgttcgctagtagtgcca tggcgtggttccgccaggctccaggaaaggagcgtgagtttgtagcgtcg ataagctaccgtggtattaccacatattatgcgcaacccgtgaagggccg attcaccatgtccagagacaatgccaagaacacggtgtatctgcaaatga acagcctgaaacctgaggacacggccgtgtattactgctacgcaaaatct atctgggtaatgcctactggggccagggaccaggtcaccgtctcgcc agaacccaagacaccaaaaccacaatcggcctctgcggcc
                                        (SEQ ID NO: 55)
cagttgcagctcgtggagcctggggaggtgtggtgcagccggggggtc tctgagactttcctgtttagcctctggaagcgacttcagtctcggtgcca tgggctggtatcgccaggcgccagggaaacagcgcgagctggtcgccatt attaatcgggcttcttggacacgttatgcagactccgtgaagggccgctt caccatctccagagacaattccaagaacttggtgtttctgcaaatgaaca acctgaaacctgacgacacagccgtctattactgtaatgcaatagcgacc agcgcgtcggggcgcggggtcacgtcgacttcgtggggccaggggtctca ggtcaccgtctcctcggaacccaagacaccaaaaccacaatcggcctctg cggcc
                                        (SEQ ID NO: 56)
atggctgaggtgcagctcgtggagtctggggggaggattggtgcaggctgg gggctctctgagactctcctgcgcagtctctggacgcacctccagtcgtt atgtcatgggctgggtccgccaggctcccgggaaggagcgtgagtttctg gcagctattagctggagtgctggctacacattctatcgagactccgtgaa gggccgattcaccatctcccgagacaacgccaagaacacggtgtatctgc aaatgaacagcctgaaacctgaggacacggccgtatattactgcaatgca gatgagaacgggttgggccggaagaggggctttggttcctggggccaggg gacccaggtcaccgtctcctcggaacccaagacaccaaaaccacaatcgg cctctgcggcc
```

(SEQ ID NO: 57)
atggctgagttgcagctcgtggagtctgggggaggagcggtgcacactgg gggctctctgaggctctcctgtgcagtatcgggacgcaccgatattcgct atgccatgggctggttccgccaggctccagggagggagcgtgagtttgta gccgctattagctggaatggtgatgatacattttatgcggattccgtgaa gggccgattcaccatctccagggacaacgccaagaacgcggtgtctctac aaatggacagcctgagacctgaggacacggccgtctattactgcaatgcg cgcaacagctacgccgccttcgcgcgtgcctactggggccaggggaccca ggtcaccgtctcctcagaacccaagacaccaaaaccacaatcggcctctg cggcc (SEQ ID NO: 58)
atggctcagttgcagctcgtggagtctgggggaggcaggtgcagcctggg gggtctctgagactctcctgtgcagcctctggattcactttggattatta tgccataggctggttccgccaggctccagggaacgagcgtgagtttgtag cagctattagctggaatggtggtagcacatactatgcagactccgtgaag ggccgattcaccatttccagagacaacgccaaggagacagtatatctgca aatgaacagcctgaagcctgaggacacaggtgtctattactgtaattata gaccacaatttggcctgggatataactattggggccaggggacccaggtc accgtctcctcagaacccaagacaccaaaaccacaatcggcctctgcggc
c The proteins synthesized from the DNA sequences represented by SEQ ID NO: 53-SEQ ID NO: 58 consist of the following amino acid sequences.

(SEQ ID NO: 38)
Gln Val Gln Leu Val Glu Ser Gly Gly Gly Val Val Gln Thr Gly Gly Ser Leu
Arg Leu Ser Cys Ala Ala Ser Gly Ser Thr Phe Ser Ile Gly Ala Met Gly Trp Tyr Arg
Gln Ala Pro Gly Lys Gln Arg Glu Leu Val Ala Thr Val Asn Arg Ala Ser Arg Thr Ile
Tyr Ala Asp Ser Val Arg Gly Arg Phe Thr Ile Ser Arg Asp Asn Ala Lys Asn Leu Val
Tyr Leu Gln Met Asn Asn Leu Lys Pro Glu Asp Thr Ala Val Tyr Tyr Cys Asn Val Ile
Ala Thr Ser Ala Ser Gly Arg Gly Val Thr Ser Thr Ser Trp Gly Gln Gly Ser Gln Val
Thr Val Ser Ser Glu Pro Lys Thr Pro Lys Pro Gln Ser Ala Ser Ala Ala (SEQ ID NO: 39)
Gln Leu Gln Leu Val Gln Ser Gly Gly Gly Leu Val Gln Ala Gly Gly Ser Leu
Arg Leu Ser Cys Val Ala Ser Gly Phe Pro Phe Ala Ser Ser Ala Met Ala Trp Phe Arg
Gln Ala Pro Gly Lys Glu Arg Gln Phe Val Ala Ser Ile Ser Tyr Arg Gly Ile Thr Thr
Tyr Tyr Ala Gln Pro Val Lys Gly Arg Phe Thr Met Ser Arg Asp Asn Ala Lys Asn Thr
Val Tyr Leu Gln Met Asn Ser Leu Lys Pro Gln Asp Thr Ala Val Tyr Tyr Cys Tyr Ala
Lys Ser Ile Trp Gly Asn Ala Tyr Trp Gly Gln Gly Thr Gln Val Thr Val Ser Pro Glu
Pro Lys Thr Pro Lys Pro Gln Ser Ala Ser Ala Ala (SEQ ID NO: 40)
Gln Leu Gln Leu Val Gln Pro Gly Gly Gly Val Val Gln Pro Gly Gly Ser Leu
Arg Leu Ser Cys Leu Ala Ser Gly Ser Asp Phe Ser Leu Gly Ala Met Gly Trp Tyr Arg
Gln Ala Pro Gly Lys Gln Arg Glu Leu Val Ala Ile Ile Asn Arg Ala Ser Trp Thr Arg
Tyr Ala Asp Ser Val Lys Gly Arg Phe Thr Ile Ser Arg Asp Asn Ser Lys Asn Leu Val
Phe Leu Gln Met Asn Asn Leu Lys Pro Asp Asp Thr Ala Val Tyr Tyr Cys Asn Ala Ile
Ala Thr Ser Ala Ser Gly Arg Gly Val Thr Ser Thr Ser Trp Gly Gln Gly Ser Gln Val
Thr Val Ser Ser Gln Pro Lys Thr Pro Lys Pro Gln Ser Ala Ser Ala Ala (SEQ ID NO: 41)
Met Ala Gln Val Gln Leu Val Glu Ser Gly Gly Gly Leu Val Gln Ala Gly Gly
Ser Leu Arg Leu Ser Cys Ala Val Ser Gly Arg Thr Ser Ser Arg Tyr Val Met Gly Trp
Val Arg Gln Ala Pro Gly Lys Gln Arg Gln Phe Leu Ala Ala Ile Ser Trp Ser Ala Gly
Tyr Thr Phe Tyr Arg Asp Ser Val Lys Gly Arg Phe Thr Ile Ser Arg Asp Asn Ala Lys
Asn Thr Val Tyr Leu Gln Met Asn Ser Leu Lys Pro Glu Asp Thr Ala Val Tyr Tyr Cys

-continued

Asn Ala Asp Glu Asn Gly Leu Gly Arg Lys Arg Gly Phe Gly Ser Trp Gly Gln Gly Thr

Gln Val Thr Val Ser Ser Gln Pro Lys Ser Ala Ala (SEQ ID NO: 42)
Met Ala Gln Leu Gln Leu Val Gln Ser Gly Gly Gty Ala Val His Thr Gly Gly

Ser Leu Arg Leu Ser Cys Ala Val Ser Gly Arg Thr Ser Ser Arg Tyr Ala Met Gly Trp

Phe Arg Gln Ala Pro Gly Arg Gln Arg Gln Phe Val Ala Ala Ile Ser Trp Asn Gly Asp

Asp Thr Phe Tyr Ala Asp Ser Val Lys Gly Arg Phe Thr Ile Ser Arg Asp Asn Ala Lys

Asn Ala Val Ser Leu Gln Met Asp Ser Leu Arg Pro Gln Asp Thr Ala Val Tyr Tyr Cys

Asn Ala Arg Asn Ser Tyr Ala Ala Phe Ala Arg Ala Tyr Trp Gly Gln Gly Thr Gln Val

Thr Val Ser Ser Gln Pro Lys Thr Pro Lys Pro Gln Ser Ala Ser Ala Ala (SEQ ID NO: 43)
Met Ala Gln Leu Gln Leu Val Gln Ser Gly Gly Gly Leu Val Gln Pro Gly Gly

Ser Leu Arg Leu Ser Cys Ala Ala Ser Gly Phe Thr Leu Asp Tyr Tyr Ala Ile Gly Trp

Phe Arg Gln Ala Pro Gly Asn Gln Arg Gln Phe Val Ala Ala Ile Ser Trp Asn Gly Gly

Ser Thr Tyr Tyr Ala Asp Ser Val Lys Gly Arg Phe Thr Ile Ser Arg Asp Asn Ala Lys

Gln Thr Val Tyr Leu Gln Met Asn Ser Leu Lys Pro Gln Asp Thr Gly Val Tyr Tyr Cys

Asn Tyr Arg Pro Gln Phe Gly Leu Gly Tyr Asn Tyr Trp Gly Gln Gly Thr Gln Val Thr

Val Ser Ser Gln Pro Lys Thr Pro Lys Pro Gln Ser Ala Ser Ala Ala (Expression of Anti-Norovirus VHH Antibody)

Figure 2:
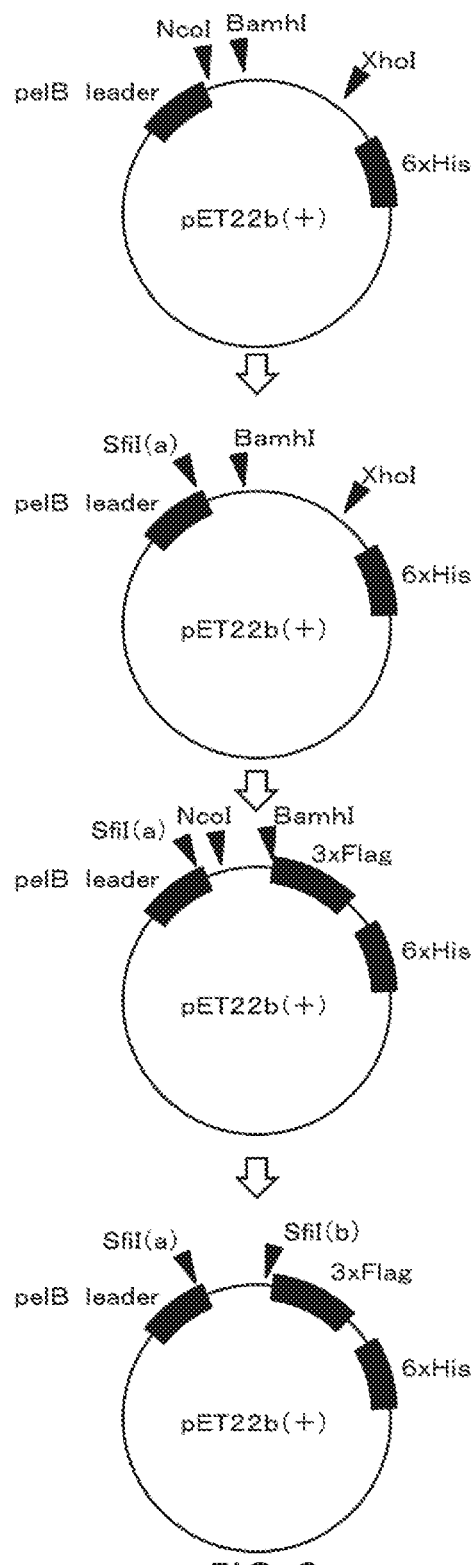
FIG. 2 shows a synthesis procedure of a vector used to express the VHH antibody.

A vector pET22b(+) was purchased from Merck Millipore Company. Using PrimeStar Mutagenesis Basal Kit (available from Takara Bio Inc.), a 3×Flag tag and two restriction enzyme sites SfiI(a) and SfiI(b) were added to the vector pET22b(+) by a PCR method. See FIG. 2. The procedure shown in FIG. 2 will be described below in more detail.

First, the restriction enzyme site SfiI(a) was add to the vector pET22b(+) by a PCR method using the following two primers and a restriction enzyme (available from Takara Bio Inc., trade name: PrimeSTAR Max DNA polymerase).

```
Primer 1:
                                    (SEQ ID NO: 59)
5'-GCCGGCTGGGCcGCGAGGAGCAGCAGACCA-3'

Primer 2:
                                    (SEQ ID NO: 60)
5'-GCCCAGCCGGCcATGGCCATGGATATCGGA-3'
```

Then, a 3×Flag tag DNA fragment having restriction enzyme sites BamhI and XhoI at 5'-terminal end and 3'-terminal end, respectively, was formed by a PCR method using the following two primers and restriction enzymes (available from Takara Bio Inc., trade name: PrimeSTAR Max DNA polymerase).

```
Primer 1:
                                    (SEQ ID NO: 61)
5'-CATGGATATCGGAATTAATTCggatccGACTACAAAGACCATGACGG
TGATTATAAAGATCATGACATatcgagCACCACCACCACCACCACTGA-
3'

Primer 2:
                                    (SEQ ID NO: 62)
5'-TCAGTGGTGGTGGTGGTGGTGctcgagGATGTCATGATCTTTATAAT
CACCGTCATGGTCTTTGTAGTCggatccGAATTAATTCCGATATCCATG-
3'
```

This 3×Flag tag DNA fragment and the vector pET22b(+) were treated with two restriction enzymes BamhI and XhoI (available from Takara Bio Inc.)

The 3×Flag tag DNA fragment was ligated into the vector pET22b(+) using Ligation Kit (available from Takara Bio Inc.). In this way, obtained was the vector pET22b(+) to which the 3×Flag tag and the restriction enzyme site SfiI(a) were added.

A DNA fragment having restriction enzyme sites NcoI and BamhI at 5'-terminal end and 3'-terminal end, respectively, was formed by a PCR method using the following two primers and restriction enzymes (available from Takara Bio Inc., trade name: PrimeSTAR Max DNA polymerase).

```
Primer 1:
                                    (SEQ ID NO: 63)
5'-AAATACCTGCTGCCGccatggATATCGGAATTAATTCggcctctgcg
gccGCAggatccGACTACAAAGACCAT-3'

Primer 2:
                                    (SEQ ID NO: 64)
5'-ATGGTCTTTGTAGTCggatccTGCggccgcagaggccGAATTAATTC
CGATATccatggCGGCAGCAGGTATTT-3'
```

Then, this DNA fragment and the vector pET22b(+) were treated with two restriction enzymes NcoI and BamhI (available from Takara Bio Inc.)

This DNA fragment was ligated into the vector pET22b(+) using Ligation Kit (available from Takara Bio Inc.). In this way, provided was the vector pET22b(+) to which the 3×Flag tag and the restriction enzyme sites SfiI (a) and SfiI(b) were added.

The sequence of the vector pET22b(+) was analyzed by Greiner Company. For the analysis of the sequence, a general T7 promotor primer set was used.

Selected were the vectors pET22b(+) which were confirmed through the analysis of the sequence to have been formed as planned.

Vectors pET22b(+) included in the liquid obtained by the PCR method were purified and collected in 50 microliters of diluted water using a DNA extraction kit (available from Promega KK). The thus-collected vectors pET22b(+) was treated with the SfiI restriction enzyme.

On the other hand, the plasmid Vector 1 into which the VHH antibody gene fragment included in the gene library of the VHH antibody was ligated was treated with the SfiI restriction enzyme. In this way, provided were the following six DNAs (SEQ ID NO: 65-SEQ ID NO: 70) including the gene sequence coding for the amino acid sequences represented by SEQ ID NO: 38-SEQ ID NO: 43.

These six DNAs were treated with the SfiI restriction enzyme. Then, the thus—treated DNAs were collected by an electrocataphoresis method. Using a DNA ligation kit (available from Takara Bio Inc.), the collected DNAs (SEQ ID NO: 71-SEQ ID NO: 76) were ligated into the plasmid treated with the SfiI restriction enzyme.

The ligation solution (2.5 microliters) and coli bacteria DH5a (available from Nippon Gene, 25 microliters) were mixed on ice. The mixture solution was left at rest on the ice for six minutes. Then, the mixture solution was heated at a temperature of 42 degrees Celsius for forty five seconds. Finally, the mixture solution was left at rest on the ice for one minute. This procedure is known as a general heat shock method.

The total amount of the mixture solution was distributed onto a LBA culture medium containing ampicillin at a concentration of 100 micrograms/milliliter. The LBA culture medium was left at rest overnight at a temperature of 37 degrees Celsius.

Three colonies were selected from among the colonies formed on the LBA culture medium. The selected three colonies were incubated in the LBA culture medium (3 milliliters) overnight.

The plasmids contained in the incubated coli bacteria were extracted from the LBA culture medium using a plasmid extraction kit (available from QIAGEN, trade name: QIAprepspin miniprep kit). In order to confirm that the gene of the targeted VHH antibody was inserted in the plasmid, the sequence of the plasmid was analyzed by Greiner Company. For the analysis of the sequence, a general T7 promotor primer set was used.

Selected were plasmids which were confirmed through the analysis of the sequence to have been formed as planned.

Coli bacteria (Competent Cell BL21 (DE3) pLysS, available from Life technologies Company) were transfected with the selected plasmids by a heat shock method.

An SOC culture medium (50 microliters) was injected into the solution containing the transfected coli bacteria. Then, the coli bacteria were rescued at a temperature of 37 degrees Celsius for one hour, while shaken at 213 rpm.

Then, the coli bacteria solution was collected. The collected coli bacteria solution (5 milliliters) was distributed onto a LBA culture medium. The LBA culture medium was left at rest overnight at a temperature of 37 degrees Celsius.

One colony was selected from among the colonies formed in the LBA culture medium. The selected colony was picked up with a toothpick. The picked-up colony was incubated in a LBA culture medium (3 milliliters) at a temperature of 37 degrees Celsius, while shaken at 213 rpm. In this way, a culture liquid was provided.

In addition, the culture liquid (25 milliliters) was mixed with a LBA culture medium (500 milliliters). Until the absorbance of the mixture solution at a wavelength of 600 nanometers reached 0.5, the mixture solution was shaken at 160 rpm at a temperature of 37 degrees Celsius.

After the absorbance reached 0.5, an isopropylthiogalactoside solution (hereinafter, referred to as "IPTG solution") was added to the mixture solution. The final concentration of the IPTG solution was 1 mM. The coli bacteria contained in the mixture solution were incubated at a temperature of 37 degrees Celsius for six hours. In order to collect the thus-incubated coli bacteria, the mixture solution was subjected to centrifugation at 6,000 rpm for ten minutes at a temperature of 4 degrees Celsius.

The collected coli bacteria were mixed with ten times its volume of PBS. The mixture solution was stirred with a vortex mixer. In this way, the coli bacteria were washed. Then, the mixture solution was subjected to centrifugation at 6,000 rpm for ten minutes at a temperature of 4 degrees Celsius to collect coli bacteria. The collected coli bacteria were mixed again with ten times its volume of PBS. The coli bacteria contained in the mixture solution were disintegrated with an ultrasonic wave.

The disintegration liquid containing coli bacteria was subjected to centrifugation at 10,000 rpm for fifteen minutes at a temperature of 4 degrees Celsius. The supernatant was collected. The collected supernatant was filtered through a 0.45-micrometer filter.

The filtrate was purified with His-trap (available from GE Healthcare) in accordance with the recommended protocol. In the purification, an elution buffer having a total amount of 3 microliters was used for 1 milliliter of the filtrate. The buffer solution contained in the filtrate was substituted with PBS, using PD-10 (available from GE Healthcare). In the substitution, PBS having a total amount of 2.5 microliters was used for 1 milliliter of the filtrate. In this way, a solution containing the Will antibody was provided.

The VHH antibody contained in the thus-provided solution was quantified with an absorption spectrometer (available from Scrum Inc., trade name: nanodrop) on the basis of the absorption measurement value at a wavelength of 280 nanometers. As a result, the concentration of the VHH antibody was 4 milligrams/milliliter.

(D-1) Surface Plasmon Resonance Evaluation of VHH Antibody Using Noro Antigen

The VHH antibody was evaluated as below using the noro antigen and a surface plasmon resonance evaluation device. The details of the surface plasmon resonance (hereinafter, referred to as "SPR") will be described below.

SPR evaluation device: T200 (available from GE Healthcare)

Immobilization buffer: HBS-EP (available from GE Healthcare)

Running buffer: HBS-EP+ (available from GE Healthcare)

Sensor chip: CM5 (available from GE Healthcare)

Immobilization reagents: N-hydroxysuccinimide (NHS) and N-[3-(dimethylamino)propyl]-N'-ethylcarbodiimide (EDC)

Noro Antigen

The noro antigen was immobilized in accordance with the wizard included in the control software of the SPR evaluation device T200. For the immobilization of the noro antigen, the noro antigen was diluted with an acetic acid solution having a pH of 4.5 and was used at a concentration of 50 microgram/milliliter. The acetic acid solution had a concentration of 1 microgram/milliliter.

Figure 3:
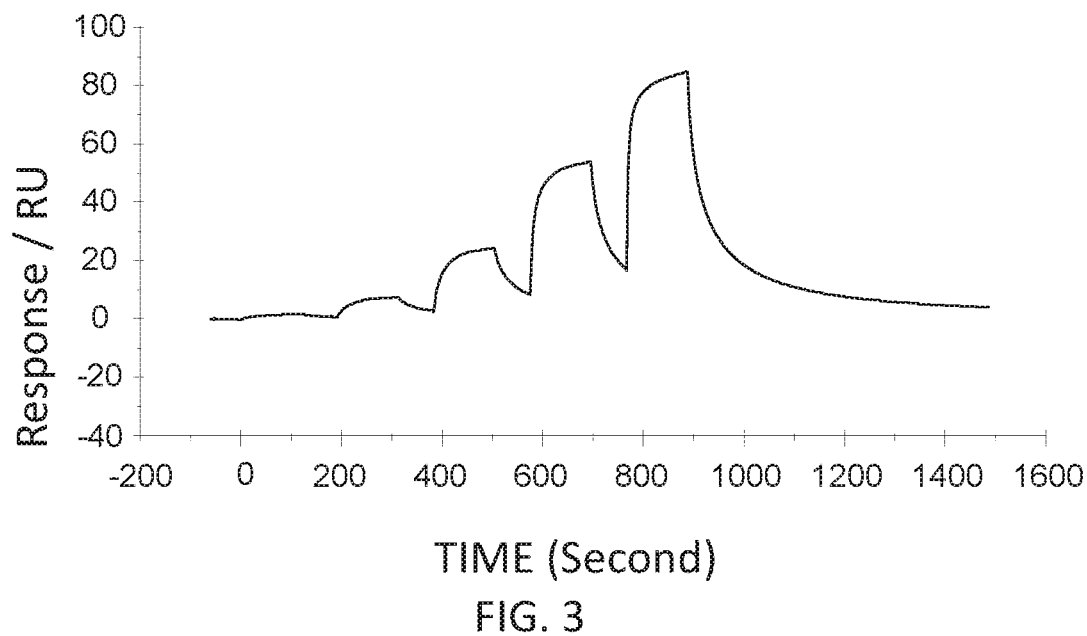
FIG. 3 is a graph showing a SPR evaluation result of the binding ability of the VHH antibody including the amino acid sequence represented by SEQ ID NO: 38 to a noro antigen, the SPR evaluation result being provided by serially adding the VHH antibodies prepared so as to have a concentration of 1.6 nM, 8 nM, 40 nM, 200 nM, and 1000 nM.
Figure 4:
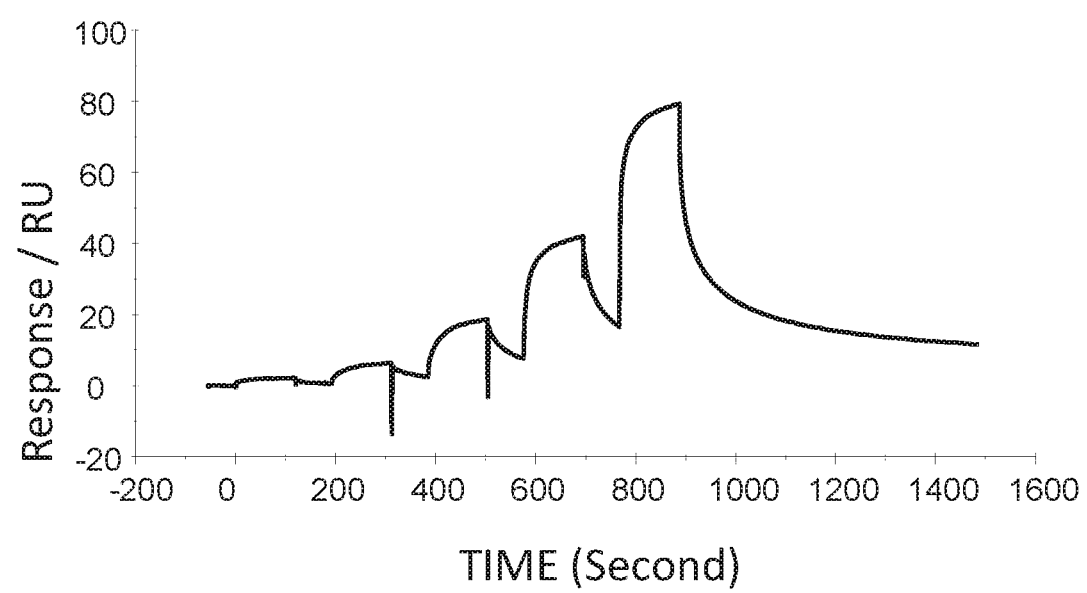
FIG. 4 is a graph showing a SPR evaluation result of the binding ability of the VHH antibody including the amino acid sequence represented by SEQ ID NO: 39 to a noro antigen, the SPR evaluation result being provided by serially adding the VHH antibodies prepared so as to have a concentration of 1.6 nM, 8 nM, 40 nM, 200 nM, and 1000 nM.
Figure 5:
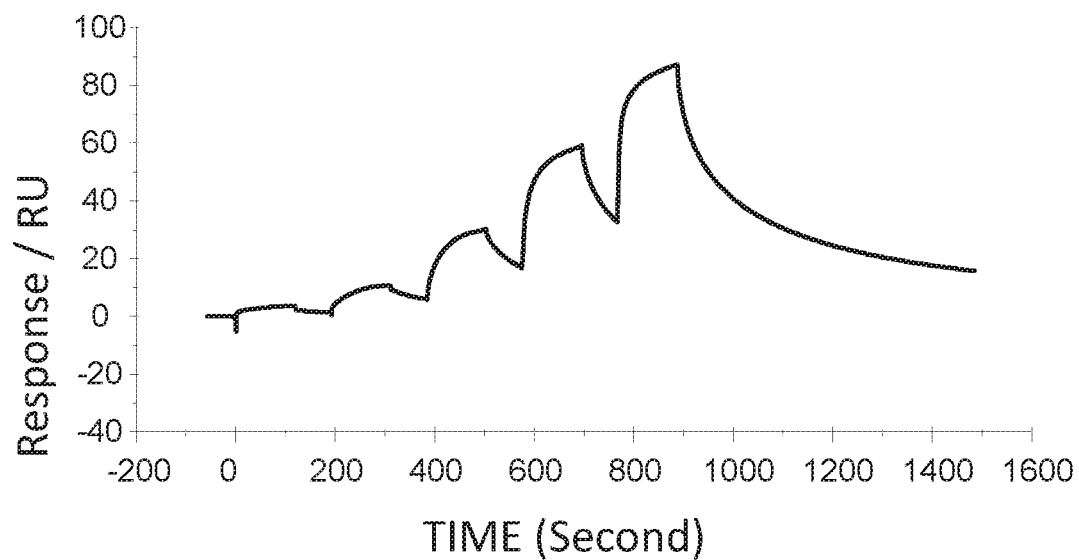
FIG. 5 is a graph showing a SPR evaluation result of the binding ability of the VHH antibody including the amino acid sequence represented by SEQ ID NO: 40 to a noro antigen, the SPR evaluation result being provided by serially adding the VHH antibodies prepared so as to have a concentration of 1.6 nM, 8 nM, 40 nM, 200 nM, and 1000 nM.
Figure 6A:
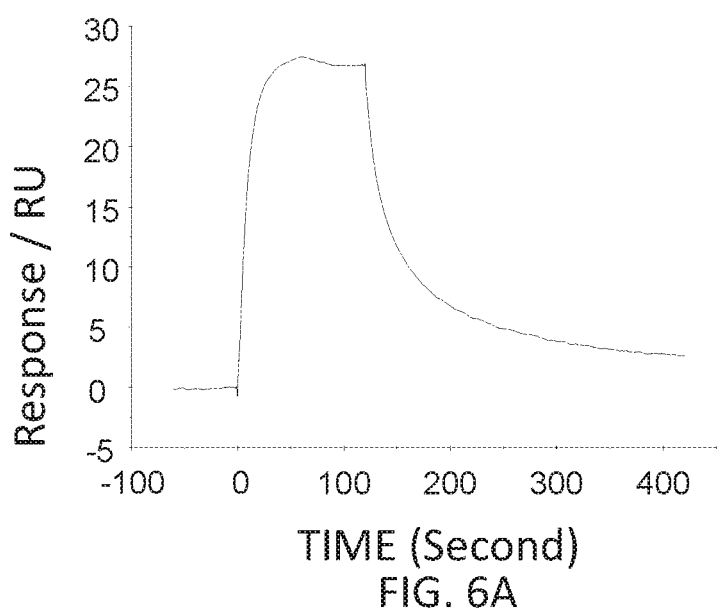
FIG. 6A is a graph showing the SPR evaluation result of the binding ability of the VHH antibody (concentration: 500 nM) including the amino acid sequence represented by SEQ ID NO: 41 to a norovirus.
Figure 6B:
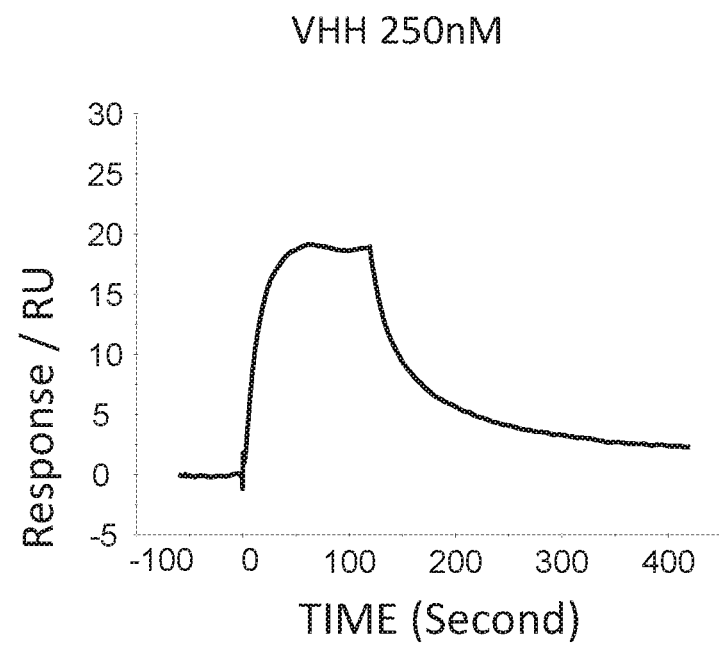
FIG. 6B is a graph showing the SPR evaluation result of the binding ability of the VHH antibody (concentration: 250 nM) including the amino acid sequence represented by SEQ ID NO: 41 to a norovirus.
Figure 6C:
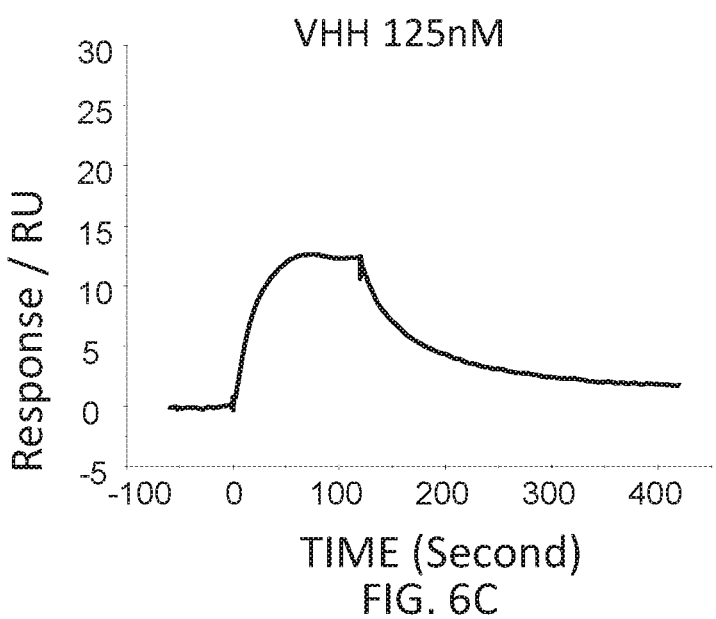
FIG. 6C is a graph showing the SPR evaluation result of the binding ability of the VHH antibody (concentration: 125 nM) including the amino acid sequence represented by SEQ ID NO: 41 to a norovirus.
Figure 6D:
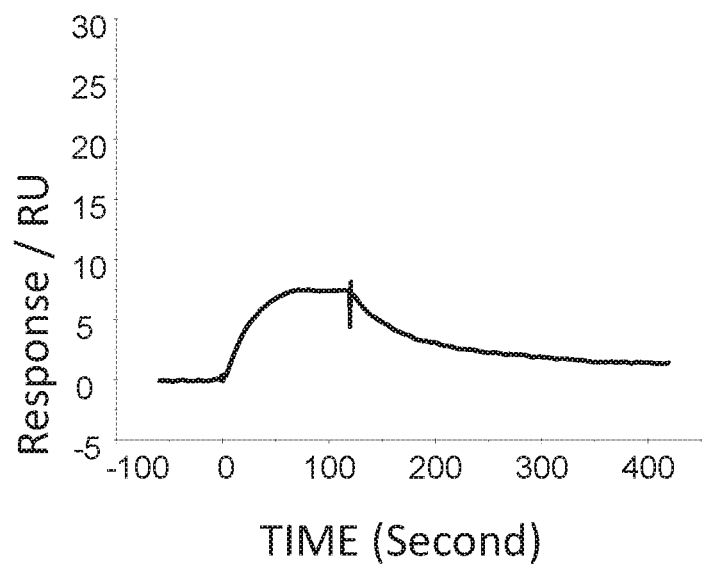
FIG. 6D is a graph showing the SPR evaluation result of the binding ability of the VHH antibody (concentration: 62.5 nM) including the amino acid sequence represented by SEQ ID NO: 41 to a norovirus
Figure 6E:
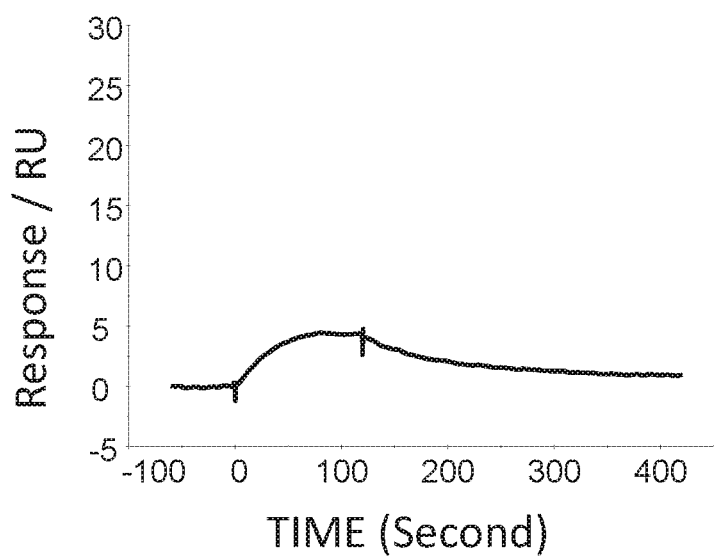
FIG. 6E is a graph showing the SPR evaluation result of the binding ability of the VHH antibody (concentration: 31.25 nM) including the amino acid sequence represented by SEQ ID NO: 41 to a norovirus.
Figure 6F:
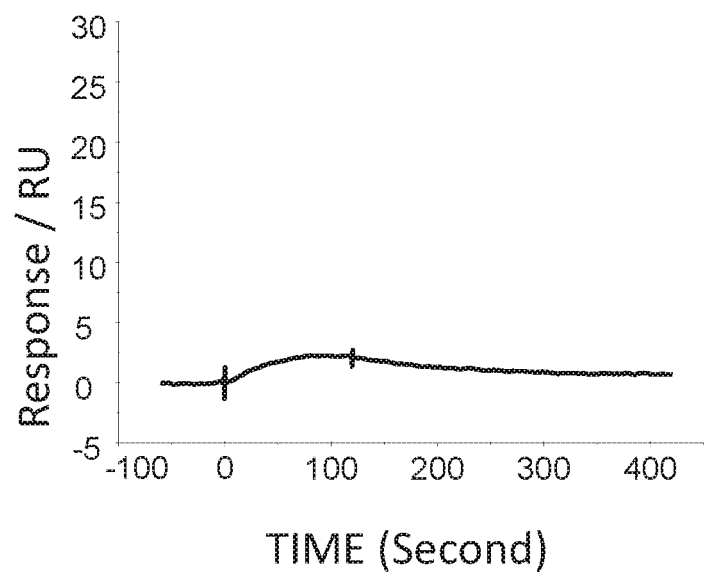
FIG. 6F is a graph showing the SPR evaluation result of the binding ability of the VHH antibody (concentration: 15.63 nM) including the amino acid sequence represented by SEQ ID NO: 41 to a norovirus.
Figure 6G:
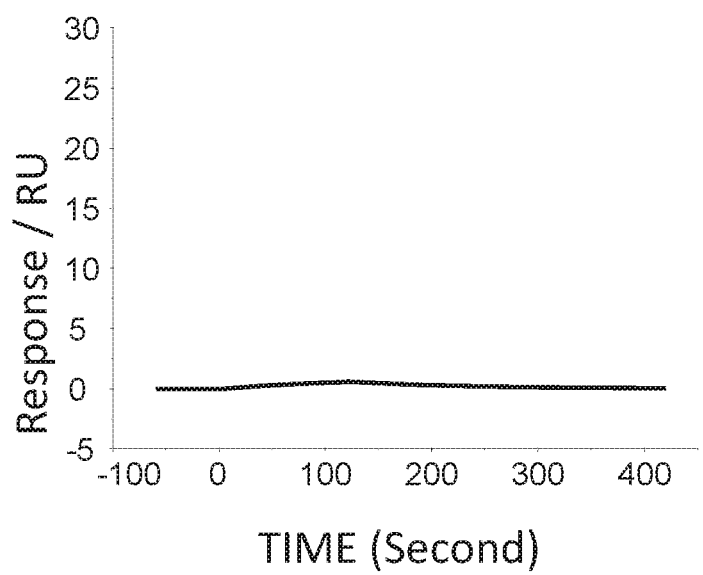
FIG. 6G is a graph showing the SPR evaluation result of the binding ability of the VHH antibody (concentration: 7.81 nM) including the amino acid sequence represented by SEQ ID NO: 41 to a norovirus

The VHH antibodies including the amino acid sequences represented by SEQ ID NO: 38-SEQ ID NO: 40 were used as analytes. The concentrations of the VHH antibodies contained in the running buffer were adjusted to 1.6 nM, 8 nM, 40 nM, 200 nM, and 1,000 nM. Then, the VHH antibodies were added serially. FIG. 3-FIG. 5 are graphs each showing evaluation result provided from the SPR evaluation device T200. The dissociation constant Kd was calculated using the evaluation software (available from GE Healthcare). As a result, the dissociation constants Kd were 1.15 nM, 15.8 nM, and 9.5 nM.

The anti-noro antibodies including the amino acid sequence represented by SEQ ID NO: 41-SEQ ID NO: 43 were used as analytes. In the first-eighth analysis, the concentrations of the anti-noro antibodies contained in the running buffer were adjusted to 500 nM, 250 nM, 125 nM, 62.5 nM, 31.25 nM, 15.63 nM, 7.81 nM, and 3.91 nM. FIG. 6A-FIG. 8H are graphs each showing evaluation result provided from the SPR evaluation device T200. The dissociation constant Kd was calculated using the evaluation software (available from GE Healthcare). As a result, the dissociation constants Kd were 81.6 nM, 63.8 nM, and 5.45 nM.

Next, the VHH antibodies (SEQ ID NO: 38-SEQ ID NO: 43) were immobilized to evaluate the binding to the noro antigen. The VHH antibodies were immobilized in accordance with the wizard included in the control software of the SPR evaluation device T200. For the immobilization of the VHH antibodies, the VHH antibodies was diluted with an acetic acid solution having a pH of 5.5 and was used at a concentration of 50 microgram/milliliter. The acetic acid solution had a concentration of 1 microgram/milliliter. The noro antigen was used as an analyte. The concentrations of the noro antigen contained in the running buffers were adjusted to 10 nM, 31.6 nM, 100 nm, 316 nM, and 1,000 nM. The running buffers were added serially. FIG. 9-FIG. 14 are graphs each showing evaluation result provided from the SPR evaluation device T200. The dissociation constant Kd was calculated using the evaluation software (available from GE Healthcare). As a result, the dissociation constants Kd were 4.15 nM, 15.9 nM, 9.57 nM, 4.98 nM, 13.1 nM, and 10.3 nM.

INDUSTRIAL APPLICABILITY

The present invention provides an antibody capable of binding to norovirus, a composite, a detection device and a method using the same.

SEQUENCE LISTING

<110> Panasonic Intellectual Property Management Co., Ltd.

SEQUENCE LISTING

```
<160> NUMBER OF SEQ ID NOS: 77

<210> SEQ ID NO 1
<211> LENGTH: 5
<212> TYPE: PRT
<213> ORGANISM: Vicugna pacos

<400> SEQUENCE: 1

Ile Gly Ala Met Gly
1               5

<210> SEQ ID NO 2
<211> LENGTH: 5
<212> TYPE: PRT
<213> ORGANISM: Vicugna pacos

<400> SEQUENCE: 2

Ser Ser Ala Met Ala
1               5

<210> SEQ ID NO 3
<211> LENGTH: 5
<212> TYPE: PRT
<213> ORGANISM: Vicugna pacos

<400> SEQUENCE: 3

Leu Gly Ala Met Gly
1               5

<210> SEQ ID NO 4
<211> LENGTH: 5
<212> TYPE: PRT
<213> ORGANISM: Vicugna pacos

<400> SEQUENCE: 4

Arg Tyr Val Met Gly
1               5

<210> SEQ ID NO 5
```

```
<211> LENGTH: 5
<212> TYPE: PRT
<213> ORGANISM: Vicugna pacos

<400> SEQUENCE: 5

Arg Tyr Ala Met Gly
1               5

<210> SEQ ID NO 6
<211> LENGTH: 5
<212> TYPE: PRT
<213> ORGANISM: Vicugna pacos

<400> SEQUENCE: 6

Tyr Tyr Ala Ile Gly
1               5

<210> SEQ ID NO 7
<211> LENGTH: 16
<212> TYPE: PRT
<213> ORGANISM: Vicugna pacos

<400> SEQUENCE: 7

Thr Val Asn Arg Ala Ser Arg Thr Ile Tyr Ala Asp Ser Val Arg Gly
1               5                   10                  15

<210> SEQ ID NO 8
<211> LENGTH: 17
<212> TYPE: PRT
<213> ORGANISM: Vicugna pacos

<400> SEQUENCE: 8

Ser Ile Ser Tyr Arg Gly Ile Thr Thr Tyr Tyr Ala Gln Pro Val Lys
1               5                   10                  15

Gly

<210> SEQ ID NO 9
<211> LENGTH: 16
<212> TYPE: PRT
<213> ORGANISM: Vicugna pacos

<400> SEQUENCE: 9

Ile Ile Asn Arg Ala Ser Trp Thr Arg Tyr Ala Asp Ser Val Lys Gly
1               5                   10                  15

<210> SEQ ID NO 10
<211> LENGTH: 17
<212> TYPE: PRT
<213> ORGANISM: Vicugna pacos

<400> SEQUENCE: 10

Ala Ile Ser Trp Ser Ala Gly Tyr Thr Phe Tyr Arg Asp Ser Val Lys
1               5                   10                  15

Gly

<210> SEQ ID NO 11
<211> LENGTH: 17
<212> TYPE: PRT
<213> ORGANISM: Vicugna pacos

<400> SEQUENCE: 11

Ala Ile Ser Trp Asn Gly Asp Asp Thr Phe Tyr Ala Asp Ser Val Lys
1               5                   10                  15
```

Gly

```
<210> SEQ ID NO 12
<211> LENGTH: 17
<212> TYPE: PRT
<213> ORGANISM: Vicugna pacos

<400> SEQUENCE: 12

Ala Ile Ser Trp Asn Gly Gly Ser Thr Tyr Tyr Ala Asp Ser Val Lys
1               5                   10                  15

Gly

<210> SEQ ID NO 13
<211> LENGTH: 14
<212> TYPE: PRT
<213> ORGANISM: Vicugna pacos

<400> SEQUENCE: 13

Ile Ala Thr Ser Ala Ser Gly Arg Gly Val Thr Ser Thr Ser
1               5                   10

<210> SEQ ID NO 14
<211> LENGTH: 8
<212> TYPE: PRT
<213> ORGANISM: Vicugna pacos

<400> SEQUENCE: 14

Lys Ser Ile Trp Gly Asn Ala Tyr
1               5

<210> SEQ ID NO 15
<211> LENGTH: 13
<212> TYPE: PRT
<213> ORGANISM: Vicugna pacos

<400> SEQUENCE: 15

Asp Glu Asn Gly Leu Gly Arg Lys Arg Gly Phe Gly Ser
1               5                   10

<210> SEQ ID NO 16
<211> LENGTH: 11
<212> TYPE: PRT
<213> ORGANISM: Vicugna pacos

<400> SEQUENCE: 16

Arg Asn Ser Tyr Ala Ala Phe Ala Arg Ala Tyr
1               5                   10

<210> SEQ ID NO 17
<211> LENGTH: 10
<212> TYPE: PRT
<213> ORGANISM: Vicugna pacos

<400> SEQUENCE: 17

Arg Pro Gln Phe Gly Leu Gly Tyr Asn Tyr
1               5                   10

<210> SEQ ID NO 18
<211> LENGTH: 30
<212> TYPE: PRT
<213> ORGANISM: Vicugna pacos

<400> SEQUENCE: 18

Gln Val Gln Leu Val Glu Ser Gly Gly Gly Val Val Gln Thr Gly Gly
```

```
1               5                   10                  15
Ser Leu Arg Leu Ser Cys Ala Ala Ser Gly Ser Thr Phe Ser
            20                  25                  30

<210> SEQ ID NO 19
<211> LENGTH: 30
<212> TYPE: PRT
<213> ORGANISM: Vicugna pacos

<400> SEQUENCE: 19

Gln Leu Gln Leu Val Glu Ser Gly Gly Gly Leu Val Gln Ala Gly Gly
1               5                   10                  15

Ser Leu Arg Leu Ser Cys Val Ala Ser Gly Phe Pro Phe Ala
            20                  25                  30

<210> SEQ ID NO 20
<211> LENGTH: 30
<212> TYPE: PRT
<213> ORGANISM: Vicugna pacos

<400> SEQUENCE: 20

Gln Leu Gln Leu Val Glu Pro Gly Gly Gly Val Val Gln Pro Gly Gly
1               5                   10                  15

Ser Leu Arg Leu Ser Cys Leu Ala Ser Gly Ser Asp Phe Ser
            20                  25                  30

<210> SEQ ID NO 21
<211> LENGTH: 30
<212> TYPE: PRT
<213> ORGANISM: Vicugna pacos

<400> SEQUENCE: 21

Glu Val Gln Leu Val Glu Ser Gly Gly Gly Leu Val Gln Ala Gly Gly
1               5                   10                  15

Ser Leu Arg Leu Ser Cys Ala Val Ser Gly Arg Thr Ser Ser
            20                  25                  30

<210> SEQ ID NO 22
<211> LENGTH: 30
<212> TYPE: PRT
<213> ORGANISM: Vicugna pacos

<400> SEQUENCE: 22

Glu Leu Gln Leu Val Glu Ser Gly Gly Gly Ala Val His Thr Gly Gly
1               5                   10                  15

Ser Leu Arg Leu Ser Cys Ala Val Ser Gly Arg Thr Asp Ile
            20                  25                  30

<210> SEQ ID NO 23
<211> LENGTH: 30
<212> TYPE: PRT
<213> ORGANISM: Vicugna pacos

<400> SEQUENCE: 23

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp
            20                  25                  30

<210> SEQ ID NO 24
<211> LENGTH: 14
<212> TYPE: PRT
```

```
<213> ORGANISM: Vicugna pacos

<400> SEQUENCE: 24

Trp Tyr Arg Gln Ala Pro Gly Lys Gln Arg Glu Leu Val Ala
1               5                   10

<210> SEQ ID NO 25
<211> LENGTH: 14
<212> TYPE: PRT
<213> ORGANISM: Vicugna pacos

<400> SEQUENCE: 25

Trp Phe Arg Gln Ala Pro Gly Lys Glu Arg Glu Phe Val Ala
1               5                   10

<210> SEQ ID NO 26
<211> LENGTH: 14
<212> TYPE: PRT
<213> ORGANISM: Vicugna pacos

<400> SEQUENCE: 26

Trp Val Arg Gln Ala Pro Gly Lys Glu Arg Glu Phe Leu Ala
1               5                   10

<210> SEQ ID NO 27
<211> LENGTH: 14
<212> TYPE: PRT
<213> ORGANISM: Vicugna pacos

<400> SEQUENCE: 27

Trp Phe Arg Gln Ala Pro Gly Arg Glu Arg Glu Phe Val Ala
1               5                   10

<210> SEQ ID NO 28
<211> LENGTH: 14
<212> TYPE: PRT
<213> ORGANISM: Vicugna pacos

<400> SEQUENCE: 28

Trp Phe Arg Gln Ala Pro Gly Asn Glu Arg Glu Phe Val Ala
1               5                   10

<210> SEQ ID NO 29
<211> LENGTH: 32
<212> TYPE: PRT
<213> ORGANISM: Vicugna pacos

<400> SEQUENCE: 29

Arg Phe Thr Ile Ser Arg Asp Asn Ala Lys Asn Leu Val Tyr Leu Gln
1               5                   10                  15

Met Asn Asn Leu Lys Pro Glu Asp Thr Ala Val Tyr Tyr Cys Asn Val
                20                  25                  30

<210> SEQ ID NO 30
<211> LENGTH: 32
<212> TYPE: PRT
<213> ORGANISM: Vicugna pacos

<400> SEQUENCE: 30

Arg Phe Thr Met Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Tyr Ala
                20                  25                  30
```

```
<210> SEQ ID NO 31
<211> LENGTH: 32
<212> TYPE: PRT
<213> ORGANISM: Vicugna pacos

<400> SEQUENCE: 31

Arg Phe Thr Ile Ser Arg Asp Asn Ser Lys Asn Leu Val Phe Leu Gln
1               5                   10                  15

Met Asn Asn Leu Lys Pro Asp Asp Thr Ala Val Tyr Tyr Cys Asn Ala
            20                  25                  30

<210> SEQ ID NO 32
<211> LENGTH: 32
<212> TYPE: PRT
<213> ORGANISM: Vicugna pacos

<400> SEQUENCE: 32

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Asn Ala
            20                  25                  30

<210> SEQ ID NO 33
<211> LENGTH: 32
<212> TYPE: PRT
<213> ORGANISM: Vicugna pacos

<400> SEQUENCE: 33

Arg Phe Thr Ile Ser Arg Asp Asn Ala Lys Asn Ala Val Ser Leu Gln
1               5                   10                  15

Met Asp Ser Leu Arg Pro Glu Asp Thr Ala Val Tyr Tyr Cys Asn Ala
            20                  25                  30

<210> SEQ ID NO 34
<211> LENGTH: 32
<212> TYPE: PRT
<213> ORGANISM: Vicugna pacos

<400> SEQUENCE: 34

Arg Phe Thr Ile Ser Arg Asp Asn Ala Lys Glu Thr Val Tyr Leu Gln
1               5                   10                  15

Met Asn Ser Leu Lys Pro Glu Asp Thr Gly Val Tyr Tyr Cys Asn Tyr
            20                  25                  30

<210> SEQ ID NO 35
<211> LENGTH: 11
<212> TYPE: PRT
<213> ORGANISM: Vicugna pacos

<400> SEQUENCE: 35

Trp Gly Gln Gly Ser Gln Val Thr Val Ser Ser
1               5                   10

<210> SEQ ID NO 36
<211> LENGTH: 11
<212> TYPE: PRT
<213> ORGANISM: Vicugna pacos

<400> SEQUENCE: 36

Trp Gly Gln Gly Thr Gln Val Thr Val Ser Pro
1               5                   10
```

```
<210> SEQ ID NO 37
<211> LENGTH: 11
<212> TYPE: PRT
<213> ORGANISM: Vicugna pacos

<400> SEQUENCE: 37

Trp Gly Gln Gly Thr Gln Val Thr Val Ser Ser
1               5                   10

<210> SEQ ID NO 38
<211> LENGTH: 135
<212> TYPE: PRT
<213> ORGANISM: Vicugna pacos

<400> SEQUENCE: 38

Gln Val Gln Leu Val Glu Ser Gly Gly Gly Val Val Gln Thr Gly Gly
1               5                   10                  15

Ser Leu Arg Leu Ser Cys Ala Ala Ser Gly Ser Thr Phe Ser Ile Gly
            20                  25                  30

Ala Met Gly Trp Tyr Arg Gln Ala Pro Gly Lys Gln Arg Glu Leu Val
        35                  40                  45

Ala Thr Val Asn Arg Ala Ser Arg Thr Ile Tyr Ala Asp Ser Val Arg
    50                  55                  60

Gly Arg Phe Thr Ile Ser Arg Asp Asn Ala Lys Asn Leu Val Tyr Leu
65                  70                  75                  80

Gln Met Asn Asn Leu Lys Pro Glu Asp Thr Ala Val Tyr Tyr Cys Asn
                85                  90                  95

Val Ile Ala Thr Ser Ala Ser Gly Arg Gly Val Thr Thr Ser Trp
            100                 105                 110

Gly Gln Gly Ser Gln Val Thr Val Ser Ser Glu Pro Lys Thr Pro Lys
        115                 120                 125

Pro Gln Ser Ala Ser Ala Ala
    130                 135

<210> SEQ ID NO 39
<211> LENGTH: 130
<212> TYPE: PRT
<213> ORGANISM: Vicugna pacos

<400> SEQUENCE: 39

Gln Leu Gln Leu Val Glu Ser Gly Gly Gly Leu Val Gln Ala Gly Gly
1               5                   10                  15

Ser Leu Arg Leu Ser Cys Val Ala Ser Gly Phe Pro Phe Ala Ser Ser
            20                  25                  30

Ala Met Ala Trp Phe Arg Gln Ala Pro Gly Lys Glu Arg Glu Phe Val
        35                  40                  45

Ala Ser Ile Ser Tyr Arg Gly Ile Thr Thr Tyr Tyr Ala Gln Pro Val
    50                  55                  60

Lys Gly Arg Phe Thr Met Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Tyr Ala Lys Ser Ile Trp Gly Asn Ala Tyr Trp Gly Gln Gly Thr Gln
            100                 105                 110

Val Thr Val Ser Pro Glu Pro Lys Thr Pro Lys Pro Gln Ser Ala Ser
        115                 120                 125

Ala Ala
    130
```

<210> SEQ ID NO 40
<211> LENGTH: 135
<212> TYPE: PRT
<213> ORGANISM: Vicugna pacos

<400> SEQUENCE: 40

Gln Leu Gln Leu Val Glu Pro Gly Gly Gly Val Val Gln Pro Gly Gly
1               5                   10                  15

Ser Leu Arg Leu Ser Cys Leu Ala Gly Ser Asp Phe Ser Leu Gly
            20                  25                  30

Ala Met Gly Trp Tyr Arg Gln Ala Pro Gly Lys Gln Arg Glu Leu Val
        35                  40                  45

Ala Ile Ile Asn Arg Ala Ser Trp Thr Arg Tyr Ala Asp Ser Val Lys
    50                  55                  60

Gly Arg Phe Thr Ile Ser Arg Asp Asn Ser Lys Asn Leu Val Phe Leu
65                  70                  75                  80

Gln Met Asn Asn Leu Lys Pro Asp Asp Thr Ala Val Tyr Tyr Cys Asn
                85                  90                  95

Ala Ile Ala Thr Ser Ala Ser Gly Arg Gly Val Thr Ser Thr Ser Trp
            100                 105                 110

Gly Gln Gly Ser Gln Val Thr Val Ser Ser Glu Pro Lys Thr Pro Lys
        115                 120                 125

Pro Gln Ser Ala Ser Ala Ala
    130                 135

<210> SEQ ID NO 41
<211> LENGTH: 137
<212> TYPE: PRT
<213> ORGANISM: Vicugna pacos

<400> SEQUENCE: 41

Met Ala Glu Val Gln Leu Val Glu Ser Gly Gly Gly Leu Val Gln Ala
1               5                   10                  15

Gly Gly Ser Leu Arg Leu Ser Cys Ala Val Ser Gly Arg Thr Ser Ser
            20                  25                  30

Arg Tyr Val Met Gly Trp Val Arg Gln Ala Pro Gly Lys Glu Arg Glu
        35                  40                  45

Phe Leu Ala Ala Ile Ser Trp Ser Ala Gly Tyr Thr Phe Tyr Arg Asp
    50                  55                  60

Ser Val Lys Gly Arg Phe Thr Ile Ser Arg Asp Asn Ala Lys Asn Thr
65                  70                  75                  80

Val Tyr Leu Gln Met Asn Ser Leu Lys Pro Glu Asp Thr Ala Val Tyr
                85                  90                  95

Tyr Cys Asn Ala Asp Glu Asn Gly Leu Gly Arg Lys Arg Gly Phe Gly
            100                 105                 110

Ser Trp Gly Gln Gly Thr Gln Val Thr Val Ser Ser Glu Pro Lys Thr
        115                 120                 125

Pro Lys Pro Gln Ser Ala Ser Ala Ala
    130                 135

<210> SEQ ID NO 42
<211> LENGTH: 135
<212> TYPE: PRT
<213> ORGANISM: Vicugna pacos

<400> SEQUENCE: 42

Met Ala Glu Leu Gln Leu Val Glu Ser Gly Gly Gly Ala Val His Thr
1               5                   10                  15

Gly Gly Ser Leu Arg Leu Ser Cys Ala Val Ser Gly Arg Thr Asp Ile
            20                  25                  30

Arg Tyr Ala Met Gly Trp Phe Arg Gln Ala Pro Gly Arg Glu Arg Glu
        35                  40                  45

Phe Val Ala Ala Ile Ser Trp Asn Gly Asp Asp Thr Phe Tyr Ala Asp
    50                  55                  60

Ser Val Lys Gly Arg Phe Thr Ile Ser Arg Asp Asn Ala Lys Asn Ala
65                  70                  75                  80

Val Ser Leu Gln Met Asp Ser Leu Arg Pro Glu Asp Thr Ala Val Tyr
            85                  90                  95

Tyr Cys Asn Ala Arg Asn Ser Tyr Ala Ala Phe Ala Arg Ala Tyr Trp
        100                 105                 110

Gly Gln Gly Thr Gln Val Thr Val Ser Ser Glu Pro Lys Thr Pro Lys
            115                 120                 125

Pro Gln Ser Ala Ser Ala Ala
    130                 135

<210> SEQ ID NO 43
<211> LENGTH: 134
<212> TYPE: PRT
<213> ORGANISM: Vicugna pacos

<400> SEQUENCE: 43

Met Ala Gln Leu Gln Leu Val Glu Ser Gly Gly Gly Leu Val Gln Pro
1               5                   10                  15

Gly Gly Ser Leu Arg Leu Ser Cys Ala Ala Ser Gly Phe Thr Leu Asp
            20                  25                  30

Tyr Tyr Ala Ile Gly Trp Phe Arg Gln Ala Pro Gly Asn Glu Arg Glu
        35                  40                  45

Phe Val Ala Ala Ile Ser Trp Asn Gly Gly Ser Thr Tyr Tyr Ala Asp
    50                  55                  60

Ser Val Lys Gly Arg Phe Thr Ile Ser Arg Asp Asn Ala Lys Glu Thr
65                  70                  75                  80

Val Tyr Leu Gln Met Asn Ser Leu Lys Pro Glu Asp Thr Gly Val Tyr
            85                  90                  95

Tyr Cys Asn Tyr Arg Pro Gln Phe Gly Leu Gly Tyr Asn Tyr Trp Gly
        100                 105                 110

Gln Gly Thr Gln Val Thr Val Ser Ser Glu Pro Lys Thr Pro Lys Pro
            115                 120                 125

Gln Ser Ala Ser Ala Ala
    130

<210> SEQ ID NO 44
<211> LENGTH: 540
<212> TYPE: PRT
<213> ORGANISM: Vicugna pacos

<400> SEQUENCE: 44

Met Lys Met Ala Ser Asn Asp Ala Asn Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

-continued

```
Asp Pro Trp Ile Arg Asn Asn Phe Val Gln Ala Pro Gly Gly Glu Phe
    50                  55                  60
Thr Val Ser Pro Arg Asn Ala Pro Gly Glu Ile Leu Trp Ser Ala Pro
 65                 70                  75                  80
Leu Gly Pro Asp Leu Asn Pro Tyr Leu Ser His Leu Ala Arg Met Tyr
                 85                  90                  95
Asn Gly Tyr Ala Gly Gly Phe Glu Val Gln Val Ile Leu Ala Gly Asn
            100                 105                 110
Ala Phe Thr Ala Gly Lys Ile Ile Phe Ala Ala Val Pro Pro Asn Phe
        115                 120                 125
Pro Thr Glu Gly Leu Ser Pro Ser Gln Val Thr Met Phe Pro His Ile
    130                 135                 140
Ile Val Asp Val Arg Gln Leu Glu Pro Val Leu Ile Pro Leu Pro Asp
145                 150                 155                 160
Val Arg Asn Asn Phe Tyr His Tyr Asn Gln Ser Asn Asp Pro Thr Ile
                165                 170                 175
Lys Leu Ile Ala Met Leu Tyr Thr Pro Leu Arg Ala Asn Asn Ala Gly
            180                 185                 190
Asp Asp Val Phe Thr Val Ser Cys Arg Val Leu Thr Arg Pro Ser Pro
        195                 200                 205
Asp Phe Asp Phe Ile Phe Leu Val Pro Pro Thr Val Glu Ser Arg Thr
    210                 215                 220
Lys Pro Phe Ser Val Pro Val Leu Thr Val Glu Glu Met Thr Asn Ser
225                 230                 235                 240
Arg Phe Pro Ile Pro Leu Glu Lys Leu Phe Thr Gly Pro Ser Ser Ala
                245                 250                 255
Phe Val Val Gln Pro Gln Asn Gly Arg Cys Thr Thr Asp Gly Val Leu
            260                 265                 270
Leu Gly Thr Thr Gln Leu Ser Pro Val Asn Ile Cys Thr Phe Arg Gly
        275                 280                 285
Asp Val Thr His Ile Thr Gly Ser Arg Asn Tyr Thr Met Asn Leu Ala
    290                 295                 300
Ser Gln Asn Trp Asn Ser Tyr Asp Pro Thr Glu Glu Ile Pro Ala Pro
305                 310                 315                 320
Leu Gly Thr Pro Asp Phe Val Gly Lys Ile Gln Gly Val Leu Thr Gln
                325                 330                 335
Thr Thr Arg Thr Asp Gly Ser Thr Arg Gly His Lys Ala Thr Val Tyr
            340                 345                 350
Thr Gly Ser Ala Asp Phe Ser Pro Lys Leu Gly Arg Val Gln Phe Ala
        355                 360                 365
Thr Asp Thr Asp Asn Asp Phe Glu Thr Asn Gln Asn Thr Lys Phe Thr
    370                 375                 380
Pro Val Gly Val Ile Gln Asp Gly Gly Thr Thr His Arg Asn Glu Pro
385                 390                 395                 400
Gln Gln Trp Val Leu Pro Ser Tyr Ser Gly Arg Asn Thr His Asn Val
                405                 410                 415
His Leu Ala Pro Ala Val Ala Pro Thr Phe Pro Gly Glu Gln Leu Leu
            420                 425                 430
Phe Phe Arg Ser Thr Met Pro Gly Cys Ser Gly Tyr Pro Asn Met Asp
        435                 440                 445
Leu Asp Cys Leu Leu Pro Gln Glu Trp Val Gln Tyr Phe Tyr Gln Glu
    450                 455                 460
Ala Ala Pro Ala Gln Ser Asp Val Ala Leu Leu Arg Phe Val Asn Pro
```

```
                465                 470                 475                 480
            Asp Thr Gly Arg Val Leu Phe Glu Cys Lys Leu His Lys Ser Gly Tyr
                            485                 490                 495

Val Thr Val Ala His Thr Gly Gln His Asp Leu Val Ile Pro Pro Asn
                        500                 505                 510

Gly Tyr Phe Arg Phe Asp Ser Trp Val Asn Gln Phe Tyr Thr Leu Ala
                    515                 520                 525

Pro Met Gly Asn Gly Thr Gly Arg Arg Arg Ala Leu
                530                 535                 540

<210> SEQ ID NO 45
<211> LENGTH: 15
<212> TYPE: DNA
<213> ORGANISM: Artificial Sequence
<220> FEATURE:
<223> OTHER INFORMATION: Primer

<400> SEQUENCE: 45
ggtggtcctg gctgc                                                          15

<210> SEQ ID NO 46
<211> LENGTH: 50
<212> TYPE: DNA
<213> ORGANISM: Artificial Sequence
<220> FEATURE:
<223> OTHER INFORMATION: Primer

<400> SEQUENCE: 46
ctgctcctcg cggcccagcc ggccatggct sagktgcagc tcgtggagtc                    50

<210> SEQ ID NO 47
<211> LENGTH: 21
<212> TYPE: DNA
<213> ORGANISM: Artificial Sequence
<220> FEATURE:
<223> OTHER INFORMATION: Primer

<400> SEQUENCE: 47
tggggtcttc gctgtggtgc g                                                   21

<210> SEQ ID NO 48
<211> LENGTH: 21
<212> TYPE: DNA
<213> ORGANISM: Artificial Sequence
<220> FEATURE:
<223> OTHER INFORMATION: Primer

<400> SEQUENCE: 48
ttgtggtttt ggtgtcttgg g                                                   21

<210> SEQ ID NO 49
<211> LENGTH: 45
<212> TYPE: DNA
<213> ORGANISM: Artificial Sequence
<220> FEATURE:
<223> OTHER INFORMATION: Primer

<400> SEQUENCE: 49
tttgctctgc ggccgcagag gccgtggggt cttcgctgtg gtgcg                         45

<210> SEQ ID NO 50
<211> LENGTH: 46
<212> TYPE: DNA
<213> ORGANISM: Artificial Sequence
```

<220> FEATURE:
<223> OTHER INFORMATION: Primer

<400> SEQUENCE: 50
tttgctctgc ggccgcagag gccgattgtg gttttggtgt cttggg           46

<210> SEQ ID NO 51
<211> LENGTH: 13
<212> TYPE: DNA
<213> ORGANISM: Artificial Sequence
<220> FEATURE:
<223> OTHER INFORMATION: SfiI(a) site

<400> SEQUENCE: 51
ggcccagccg gcc                                               13

<210> SEQ ID NO 52
<211> LENGTH: 13
<212> TYPE: DNA
<213> ORGANISM: Artificial Sequence
<220> FEATURE:
<223> OTHER INFORMATION: SfiI(b) site

<400> SEQUENCE: 52
ggcctctgcg gcc                                               13

<210> SEQ ID NO 53
<211> LENGTH: 405
<212> TYPE: DNA
<213> ORGANISM: Artificial Sequence
<220> FEATURE:
<223> OTHER INFORMATION: DNA coding for anti-Norovirus VHH antibody

<400> SEQUENCE: 53
caggtgcagc tcgtggagtc tgggggaggt gtggtgcaga ctggggggtc tctgagactt    60
tcctgtgcag cctctggaag tactttcagt atcggtgcca tgggctggta ccgccaggcg   120
ccagggaagc agcgcgagtt ggtcgccact gttaatcggg cttctcggac aatctatgca   180
gactccgtga ggggccgatt caccatctcc agagacaatg ccaagaattt ggtgtatctg   240
caaatgaaca acctgaaacc tgaggacaca gccgtctatt attgtaatgt aatagcgacc   300
agcgcgtcgg ggcgcggggt cacgtcgact tcgtggggcc aggggtctca ggtcaccgtc   360
tcctcggaac ccaagacacc aaaaccacaa tcggcctctg cggcc                  405

<210> SEQ ID NO 54
<211> LENGTH: 390
<212> TYPE: DNA
<213> ORGANISM: Artificial Sequence
<220> FEATURE:
<223> OTHER INFORMATION: DNA coding for anti-Norovirus VHH antibody

<400> SEQUENCE: 54
cagttgcagc tcgtggagtc tgggggaggc ttggtgcagg ctggggggtc tctgagactc    60
tcctgtgtag cctctggatt cccgttcgct agtagtgcca tggcgtggtt ccgccaggct   120
ccaggaaagg agcgtgagtt tgtagcgtcg ataagctacc gtggtattac cacatattat   180
gcgcaacccg tgaagggccg attcaccatg tccagagaca atgccaagaa cacggtgtat   240
ctgcaaatga acagcctgaa acctgaggac acggccgtgt attactgcta cgcaaaatct   300
atctggggta atgcctactg ggccagggg acccaggtca ccgtctcgcc agaacccaag   360
acaccaaaac cacaatcggc ctctgcggcc                                  390

<210> SEQ ID NO 55
<211> LENGTH: 405
<212> TYPE: DNA
<213> ORGANISM: Artificial Sequence
<220> FEATURE:
<223> OTHER INFORMATION: DNA coding for anti-Norovirus VHH antibody

<400> SEQUENCE: 55

```
cagttgcagc tcgtggagcc tggggggaggt gtggtgcagc cggggggggtc tctgagactt      60 tcctgtttag cctctggaag cgacttcagt ctcggtgcca tgggctggta tcgccaggcg     120
ccagggaaac agcgcgagct ggtcgccatt attaatcggg cttcttggac acgttatgca     180
gactccgtga agggccgctt caccatctcc agagacaatt ccaagaactt ggtgtttctg     240
caaatgaaca acctgaaacc tgacgacaca gccgtctatt actgtaatgc aatagcgacc     300
agcgcgtcgg ggcgcggggt cacgtcgact tcgtggggcc aggggtctca ggtcaccgtc     360
tcctcggaac ccaagacacc aaaaccacaa tcggcctctg cggcc                     405
```

<210> SEQ ID NO 56
<211> LENGTH: 411
<212> TYPE: DNA
<213> ORGANISM: Artificial Sequence
<220> FEATURE:
<223> OTHER INFORMATION: DNA coding for anti-Norovirus VHH antibody

<400> SEQUENCE: 56

```
atggctgagg tgcagctcgt ggagtctggg ggaggattgg tgcaggctgg gggctctctg      60
agactctcct gcgcagtctc tggacgcacc tccagtcgtt atgtcatggg ctgggtccgc     120
caggctcccg gaaggagcg tgagtttctg gcagctatta gctggagtgc tggctacaca     180
ttctatcgag actccgtgaa gggccgattc accatctccc cagacaacgc caagaacacg     240
gtgtatctgc aaatgaacag cctgaaacct gaggacacgg ccgtatatta ctgcaatgca     300
gatgagaacg ggttgggccg gaagagggc tttggttcct ggggccaggg gacccaggtc     360
accgtctcct cggaacccaa gacaccaaaa ccacaatcgg cctctgcggc c              411
```

<210> SEQ ID NO 57
<211> LENGTH: 405
<212> TYPE: DNA
<213> ORGANISM: Artificial Sequence
<220> FEATURE:
<223> OTHER INFORMATION: DNA coding for anti-Norovirus VHH antibody

<400> SEQUENCE: 57

```
atggctgagt tgcagctcgt ggagtctggg ggaggagcgg tgcacactgg gggctctctg      60
aggctctcct gtgcagtatc gggacgcacc gatattcgct atgccatggg ctggttccgc     120
caggctccag ggagggagcg tgagtttgta gccgctatta gctggaatgg tgatgataca     180
ttttatgcgg attccgtgaa gggccgattc accatctcca gggacaacgc caagaacgcg     240
gtgtctctac aaatggacag cctgagacct gaggacacgg ccgtctatta ctgcaatgcg     300
cgcaacagct acgccgcctt cgcgcgtgcc tactggggcc aggggaccca ggtcaccgtc     360
tcctcagaac ccaagacacc aaaaccacaa tcggcctctg cggcc                     405
```

<210> SEQ ID NO 58
<211> LENGTH: 402
<212> TYPE: DNA
<213> ORGANISM: Artificial Sequence
<220> FEATURE:
<223> OTHER INFORMATION: DNA coding for anti-Norovirus VHH antibody

<400> SEQUENCE: 58

| atggctcagt | tgcagctcgt | ggagtctggg | ggaggcttgg | tgcagcctgg | ggggtctctg | 60 |
| agactctcct | gtgcagcctc | tggattcact | ttggattatt | atgccatagg | ctggttccgc | 120 |
| caggctccag | ggaacgagcg | tgagtttgta | gcagctatta | gctggaatgg | tggtagcaca | 180 |
| tactatgcag | actccgtgaa | gggccgattc | accatttcca | gagacaacgc | caaggagaca | 240 |
| gtatatctgc | aaatgaacag | cctgaagcct | gaggacacag | tgtctatta | ctgtaattat | 300 |
| agaccacaat | ttggcctggg | atataactat | ggggccagg | ggacccaggt | caccgtctcc | 360 |
| tcagaaccca | agacaccaaa | accacaatcg | gcctctgcgg | cc | | 402 |

<210> SEQ ID NO 59
<211> LENGTH: 30
<212> TYPE: DNA
<213> ORGANISM: Artificial Sequence
<220> FEATURE:
<223> OTHER INFORMATION: Primer

<400> SEQUENCE: 59
gccggctggg ccgcgaggag cagcagacca       30

<210> SEQ ID NO 60
<211> LENGTH: 30
<212> TYPE: DNA
<213> ORGANISM: Artificial Sequence
<220> FEATURE:
<223> OTHER INFORMATION: Primer

<400> SEQUENCE: 60
gcccagccgg ccatggccat ggatatcgga       30

<210> SEQ ID NO 61
<211> LENGTH: 96
<212> TYPE: DNA
<213> ORGANISM: Artificial Sequence
<220> FEATURE:
<223> OTHER INFORMATION: Primer

<400> SEQUENCE: 61
catggatatc ggaattaatt cggatccgac tacaaagacc atgacggtga ttataaagat    60
catgacatcc tcgagcacca ccaccaccac cactga                              96

<210> SEQ ID NO 62
<211> LENGTH: 96
<212> TYPE: DNA
<213> ORGANISM: Artificial Sequence
<220> FEATURE:
<223> OTHER INFORMATION: Primer

<400> SEQUENCE: 62
tcagtggtgg tggtggtggt gctcgaggat gtcatgatct ttataatcac cgtcatggtc    60
tttgtagtcg gatccgaatt aattccgata tccatg                              96

<210> SEQ ID NO 63
<211> LENGTH: 74
<212> TYPE: DNA
<213> ORGANISM: Artificial Sequence
<220> FEATURE:
<223> OTHER INFORMATION: Primer

<400> SEQUENCE: 63

<210> SEQ ID NO 64
<211> LENGTH: 74
<212> TYPE: DNA
<213> ORGANISM: Artificial Sequence
<220> FEATURE:
<223> OTHER INFORMATION: Primer

<400> SEQUENCE: 64

```
aaatacctgc tgccgccatg gatatcggaa ttaattcggc ctctgcggcc gcaggatccg      60
actacaaaga ccat                                                        74
```

<210> SEQ ID NO 64
<211> LENGTH: 74
<212> TYPE: DNA
<213> ORGANISM: Artificial Sequence
<220> FEATURE:
<223> OTHER INFORMATION: Primer

<400> SEQUENCE: 64

```
atggtctttg tagtcggatc ctgcggccgc agaggccgaa ttaattccga tatccatggc      60
ggcagcaggt attt                                                        74
```

<210> SEQ ID NO 65
<211> LENGTH: 424
<212> TYPE: DNA
<213> ORGANISM: Artificial Sequence
<220> FEATURE:
<223> OTHER INFORMATION: DNA including the gene sequence coding for the
      amino acid sequence represented by SEQ ID NO: 38

<400> SEQUENCE: 65

```
ggcccagccg gccatggctc aggtgcagct cgtggagtct gggggaggtg tggtgcagac      60
tggggggtct ctgagacttt cctgtgcagc ctctggaagt actttcagta tcggtgccat     120
gggctggtac cgccaggcgc cagggaagca gcgcgagttg gtcgccactg ttaatcgggc     180
ttctcggaca atctatgcag actccgtgag gggccgattc accatctcca gagacaatgc     240
caagaatttg gtgtatctgc aaatgaacaa cctgaaacct gaggacacag ccgtctatta     300
ttgtaatgta atagcgacca gcgcgtcggg gcgcggggtc acgtcgactt cgtggggcca     360
ggggtctcag gtcaccgtct cctcggaacc caagacacca aaaccacaat cggcctctgc     420
ggcc                                                                  424
```

<210> SEQ ID NO 66
<211> LENGTH: 409
<212> TYPE: DNA
<213> ORGANISM: Artificial Sequence
<220> FEATURE:
<223> OTHER INFORMATION: DNA including the gene sequence coding for the
      amino acid sequence represented by SEQ ID NO: 39

<400> SEQUENCE: 66

```
ggcccagccg gccatggctc agttgcagct cgtggagtct gggggaggct tggtgcaggc      60
tggggggtct ctgagactct cctgtgtagc ctctggattc ccgttcgcta gtagtgccat     120
ggcgtggttc cgccaggctc caggaaagga gcgtgagttt gtagcgtcga taagctaccg     180
tggtattacc acatattatg cgcaacccgt gaagggccga ttcaccatgt ccagagacaa     240
tgccaagaac acggtgtatc tgcaaatgaa cagcctgaaa cctgaggaca cggccgtgta     300
ttactgctac gcaaaatcta tctggggtaa tgcctactgg ggccagggga cccaggtcac     360
cgtctcgcca gaacccaaga caccaaaacc acaatcggcc tctgcggcc                 409
```

<210> SEQ ID NO 67
<211> LENGTH: 424
<212> TYPE: DNA
<213> ORGANISM: Artificial Sequence
<220> FEATURE:
<223> OTHER INFORMATION: DNA including the gene sequence coding for the
      amino acid sequence represented by SEQ ID NO: 40

<400> SEQUENCE: 67

```
ggcccagccg gccatggctc agttgcagct cgtggagcct gggggaggtg tggtgcagcc    60
ggggggggtct ctgagacttt cctgtttagc ctctggaagc gacttcagtc tcggtgccat   120
gggctggtat cgccaggcgc cagggaaaca gcgcgagctg gtcgccatta ttaatcgggc   180
ttcttggaca cgttatgcag actccgtgaa gggccgcttc accatctcca gagacaattc   240
caagaacttg gtgtttctgc aaatgaacaa cctgaaacct gacgacacag ccgtctatta   300
ctgtaatgca atagcgacca gcgcgtcggg gcgcggggtc acgtcgactt cgtggggcca   360
ggggtctcag gtcaccgtct cctcggaacc caagacacca aaaccacaat cggcctctgc   420
ggcc                                                                 424
```

<210> SEQ ID NO 68
<211> LENGTH: 430
<212> TYPE: DNA
<213> ORGANISM: Artificial Sequence
<220> FEATURE:
<223> OTHER INFORMATION: DNA including the gene sequence coding for the
      amino acid sequence represented by SEQ ID NO: 41

<400> SEQUENCE: 68

```
ggcccagccg gccatggcta tggctgaggt gcagctcgtg gagtctgggg gaggattggt    60
gcaggctggg ggctctctga gactctcctg cgcagtctct ggacgcacct ccagtcgtta   120
tgtcatgggc tgggtccgcc aggctcccgg gaaggagcgt gagtttctgg cagctattag   180
ctggagtgct ggctacacat tctatcgaga ctccgtgaag gccgattca ccatctcccg    240
agacaacgcc aagaacacgg tgtatctgca aatgaacagc ctgaaacctg aggacacggc   300
cgtatattac tgcaatgcag atgagaacgg gttgggccgg aagagggggct ttggttcctg   360
gggccagggg acccaggtca ccgtctcctc ggaacccaag acaccaaaac cacaatcggc   420
ctctgcggcc                                                           430
```

<210> SEQ ID NO 69
<211> LENGTH: 424
<212> TYPE: DNA
<213> ORGANISM: Artificial Sequence
<220> FEATURE:
<223> OTHER INFORMATION: DNA including the gene sequence coding for the
      amino acid sequence represented by SEQ ID NO: 42

<400> SEQUENCE: 69

```
ggcccagccg gccatggcta tggctgagtt gcagctcgtg gagtctgggg gaggagcggt    60
gcacactggg ggctctctga ggctctcctg tgcagtatcg ggacgcaccg atattcgcta   120
tgccatgggc tggttccgcc aggctccagg gagggagcgt gagtttgtag ccgctattag   180
ctggaatggt gatgatacat tttatgcgga ttccgtgaag gccgattca ccatctccag   240
ggacaacgcc aagaacgcgg tgtctctaca aatggacagc ctgagacctg aggacacggc   300
cgtctattac tgcaatgcgc gcaacagcta cgccgccttc gcgcgtgcct actggggcca   360
ggggacccag gtcaccgtct cctcagaacc caagacacca aaaccacaat cggcctctgc   420
ggcc                                                                 424
```

<210> SEQ ID NO 70
<211> LENGTH: 421
<212> TYPE: DNA
<213> ORGANISM: Artificial Sequence
<220> FEATURE:
<223> OTHER INFORMATION: DNA including the gene sequence coding for the amino acid sequence represented by SEQ ID NO: 43

<400> SEQUENCE: 70

| ggcccagccg gccatggcta tggctcagtt gcagctcgtg gagtctgggg gaggcttggt | 60 |
| gcagcctggg gggtctctga gactctcctg tgcagcctct ggattcactt tggattatta | 120 |
| tgccataggc tggttccgcc aggctccagg gaacgagcgt gagtttgtag cagctattag | 180 |
| ctggaatggt ggtagcacat actatgcaga ctccgtgaag gccgattca ccatttccag | 240 |
| agacaacgcc aaggagacag tatatctgca aatgaacagc ctgaagcctg aggacacagg | 300 |
| tgtctattac tgtaattata gaccacaatt tggcctggga tataactatt ggggccaggg | 360 |
| gacccaggtc accgtctcct cagaacccaa gacaccaaaa ccacaatcgg cctctgcggc | 420 |
| c | 421 |

<210> SEQ ID NO 71
<211> LENGTH: 420
<212> TYPE: DNA
<213> ORGANISM: Artificial Sequence
<220> FEATURE:
<223> OTHER INFORMATION: SfiI-treated SEQ ID NO:65

<400> SEQUENCE: 71

| cggccatggc tcaggtgcag ctcgtggagt ctgggggagg tgtggtgcag actgggggt | 60 |
| ctctgagact ttcctgtgca gcctctggaa gtactttcag tatcggtgcc atgggctggt | 120 |
| accgccaggc gccagggaag cagcgcgagt tggtcgccac tgttaatcgg gcttctcgga | 180 |
| caatctatgc agactccgtg aggggccgat tcaccatctc cagagacaat gccagaatt | 240 |
| tggtgtatct gcaaatgaac aacctgaaac ctgaggacac agccgtctat tattgtaatg | 300 |
| taatagcgac cagcgcgtcg gggcgcgggg tcacgtcgac ttcgtggggc caggggtctc | 360 |
| aggtcaccgt ctcctcggaa cccaagacac caaaaccaca atcggcctct gcggcctctg | 420 |

<210> SEQ ID NO 72
<211> LENGTH: 405
<212> TYPE: DNA
<213> ORGANISM: Artificial Sequence
<220> FEATURE:
<223> OTHER INFORMATION: SfiI-treated SEQ ID NO:66

<400> SEQUENCE: 72

| cggccatggc tcagttgcag ctcgtggagt ctgggggagg cttggtgcag gctgggggt | 60 |
| ctctgagact ctcctgtgta gcctctggat tcccgttcgc tagtagtgcc atggcgtggt | 120 |
| tccgccaggc tccaggaaag gagcgtgagt ttgtagcgtc gataagctac cgtggtatta | 180 |
| ccacatatta tgcgcaaccc gtgaagggcc gattcaccat gtccagagac aatgccaaga | 240 |
| acacggtgta tctgcaaatg aacagcctga aacctgagga cacggccgtg tattactgct | 300 |
| acgcaaaatc tatctggggt aatgcctact ggggccaggg gacccaggtc accgtctcgc | 360 |
| cagaacccaa gacaccaaaa ccacaatcgg cctctgcggc ctctg | 405 |

<210> SEQ ID NO 73
<211> LENGTH: 420
<212> TYPE: DNA
<213> ORGANISM: Artificial Sequence
<220> FEATURE:
<223> OTHER INFORMATION: SfiI-treated SEQ ID NO:67

<400> SEQUENCE: 73

| cggccatggc tcagttgcag ctcgtggagc ctgggggagg tgtggtgcag ccgggggggt | 60 |

```
ctctgagact ttcctgttta gcctctggaa gcgacttcag tctcggtgcc atgggctggt        120
atcgccaggc gccagggaaa cagcgcgagc tggtcgccat tattaatcgg gcttcttgga        180
cacgttatgc agactccgtg aagggccgct tcaccatctc cagagacaat tccaagaact        240
tggtgtttct gcaaatgaac aacctgaaac ctgacgacag cccgtctat tactgtaatg         300 caatagcgac cagcgcgtcg gggcgcgggg tcacgtcgac ttcgtggggc caggggtctc        360
aggtcaccgt ctcctcggaa cccaagacac caaaaccaca atcggcctct gcggcctctg        420
```

<210> SEQ ID NO 74
<211> LENGTH: 426
<212> TYPE: DNA
<213> ORGANISM: Artificial Sequence
<220> FEATURE:
<223> OTHER INFORMATION: SfiI-treated SEQ ID NO:68

<400> SEQUENCE: 74

```
cggccatggc tatggctgag gtgcagctcg tggagtctgg gggaggattg gtgcaggctg         60
ggggctctct gagactctcc tgcgcagtct ctggacgcac ctccagtcgt tatgtcatgg        120
gctgggtccg ccaggctccc gggaaggagc gtgagtttct ggcagctatt agctggagtg        180
ctggctacac attctatcga gactccgtga agggccgatt caccatctcc cgagacaacg        240
ccaagaacac ggtgtatctg caaatgaaca gcctgaaacc tgaggacacg gccgtatatt        300
actgcaatgc agatgagaac gggttgggcc ggaagagggg ctttggttcc tggggccagg        360
ggacccaggt caccgtctcc tcggaaccca agacaccaaa accacaatcg gcctctgcgg        420
cctctg                                                                  426
```

<210> SEQ ID NO 75
<211> LENGTH: 420
<212> TYPE: DNA
<213> ORGANISM: Artificial Sequence
<220> FEATURE:
<223> OTHER INFORMATION: SfiI-treated SEQ ID NO:69

<400> SEQUENCE: 75

```
cggccatggc tatggctgag ttgcagctcg tggagtctgg gggaggagcg gtgcacactg         60
ggggctctct gaggctctcc tgtgcagtat cgggacgcac cgatattcgc tatgccatgg       120
gctggttccg ccaggctcca gggagggagc gtgagtttgt agccgctatt agctggaatg       180
gtgatgatac attttatgcg gattccgtga agggccgatt caccatctcc agggacaacg       240
ccaagaacgc ggtgtctcta caaatggaca gcctgagacc tgaggacacg gccgtctatt       300
actgcaatgc gcgcaacagc tacgccgcct tcgcgcgtgc ctactggggc caggggaccc       360
aggtcaccgt ctcctcagaa cccaagacac caaaaccaca atcggcctct gcggcctctg       420
```

<210> SEQ ID NO 76
<211> LENGTH: 417
<212> TYPE: DNA
<213> ORGANISM: Artificial Sequence
<220> FEATURE:
<223> OTHER INFORMATION: SfiI-treated SEQ ID NO:70

<400> SEQUENCE: 76

```
cggccatggc tatggctcag ttgcagctcg tggagtctgg gggaggcttg gtgcagcctg         60
ggggtctctc tgagactctcc tgtgcagcct ctggattcac tttggattat tatgccatag     120
gctggttccg ccaggctcca gggaacgagc gtgagtttgt agcagctatt agctggaatg       180
```

| | |
|---|---|
| gtggtagcac atactatgca gactccgtga agggccgatt caccatttcc agagacaacg | 240 |
| ccaaggagac agtatatctg caaatgaaca gcctgaagcc tgaggacaca ggtgtctatt | 300 |
| actgtaatta tagaccacaa tttggcctgg gatataacta ttggggccag gggacccagg | 360 |
| tcaccgtctc ctcagaaccc aagacaccaa aaccacaatc ggcctctgcg gcctctg | 417 |

```
<210> SEQ ID NO 77
<211> LENGTH: 4057
<212> TYPE: DNA
<213> ORGANISM: Artificial Sequence
<220> FEATURE:
<223> OTHER INFORMATION: Plasmid Vector 1

<400> SEQUENCE: 77
```

| | |
|---|---|
| gacgaaaggg cctcgtgata cgcctatttt tataggttaa tgtcatgata ataatggttt | 60 |
| cttagacgtc aggtggcact tttcggggaa atgtgcgcgg aacccctatt tgtttatttt | 120 |
| tctaaataca ttcaaatatg tatccgctca tgagacaata accctgataa atgcttcaat | 180 |
| aatattgaaa aaggaagagt atgagtattc aacatttccg tgtcgccctt attcccttt  | 240 |
| ttgcggcatt ttgccttcct gttttgctc acccagaaac gctggtgaaa gtaaaagatg | 300 |
| ctgaagatca gttgggtgca cgagtgggtt acatcgaact ggatctcaac agcggtaaga | 360 |
| tccttgagag ttttcgcccc gaagaacgtt ttccaatgat gagcactttt aaagttctgc | 420 |
| tatgtggcgc ggtattatcc cgtattgacg ccgggcaaga gcaactcggt cgccgcatac | 480 |
| actattctca gaatgacttg gttgagtact caccagtcac agaaaagcat cttacggatg | 540 |
| gcatgacagt aagagaatta tgcagtgctg ccataaccat gagtgataac actgcggcca | 600 |
| acttacttct gacaacgatc ggaggaccga aggagctaac cgcttttttg cacaacatgg | 660 |
| gggatcatgt aactcgcctt gatcgttggg aaccggagct gaatgaagcc ataccaaacg | 720 |
| acgagcgtga caccacgatg cctgtagcaa tggcaacaac gttgcgcaaa ctattaactg | 780 |
| gcgaactact tactctagct tcccggcaac aattaataga ctggatggag gcggataaag | 840 |
| ttgcaggacc acttctgcgc tcggcccttc cggctggctg gtttattgct gataaatctg | 900 |
| gagccggtga gcgtgggtct cgcggtatca ttgcagcact ggggccagat ggtaagccct | 960 |
| cccgtatcgt agttatctac acgacgggga gtcaggcaac tatggatgaa cgaaatagac | 1020 |
| agatcgctga gataggtgcc tcactgatta agcattggta actgtcagac caagtttact | 1080 |
| catatatact ttagattgat ttaaaacttc atttttaatt taaaaggatc taggtgaaga | 1140 |
| tcctttttga taatctcatg accaaaatcc cttaacgtga gttttcgttc cactgagcgt | 1200 |
| cagaccccgt agaaaagatc aaaggatctt cttgagatcc tttttttctg cgcgtaatct | 1260 |
| gctgcttgca acaaaaaaa ccaccgctac cagcggtggt ttgtttgccg gatcaagagc | 1320 |
| taccaactct tttccgaag gtaactggct tcagcagagc gcagatacca aatactgtcc | 1380 |
| ttctagtgta gccgtagtta ggccaccact tcaagaactc tgtagcaccg cctacatacc | 1440 |
| tcgctctgct aatcctgtta ccagtggctg ctgccagtgg cgataagtcg tgtcttaccg | 1500 |
| ggttggactc aagacgatag ttaccggata aggcgcagcg gtcgggctga acggggggtt | 1560 |
| cgtgcacaca gcccagcttg gagcgaacga cctacaccga actgagatac ctacagcgtg | 1620 |
| agctatgaga aagcgccacg cttcccgaag ggagaaaggc ggacaggtat ccggtaagcg | 1680 |
| gcagggtcgg aacaggagag cgcacgaggg agcttccagg gggaaacgcc tggtatcttt | 1740 |
| atagtcctgt cgggtttcgc cacctctgac ttgagcgtcg atttttgtga tgctcgtcag | 1800 |
| gggggcggag cctatggaaa aacgccagca acgcggcctt tttacggttc ctggccttt  | 1860 |

```
gctggccttt tgctcacatg ttctttcctg cgttatcccc tgattctgtg gataaccgta   1920
ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttag ctcactcatt aggcacccca ggctttacac tttatgcttc   2160
cggctcgtat gttgtgtgga attgtgagcg gataacaatt tcacacagga aacagctatg   2220
accatgatta cgccaagctt cgaaggagac agtcataatg aaataccctgc tgccgaccgc   2280 tgctgctggt ctgctgctcc tcgcggccca gccggccatg gagctcaaga tgacacagac   2340
tacatcctcc ctgtcagcct ctctgggaga cagagtcacc atcagttgca gggcaagtca   2400
ggacattagc gattatttaa actggtatca gcagaaacca gatggaactg ttaaactcct   2460
gatctattac acatcaagtt tacactcagg agtcccatca aggttcagtg gcggtgggtc   2520
tggaacagat tattctctca ccattagcaa cctggagcaa aagatatttg ccacttactt   2580 tgccaacag  ggtaatacgc ttccgtggac gtttggtgga ggcaccaagc tggaaatcaa   2640
acgggctgat gctgcaccaa ctgtaggcct ctgcggccgc agagcaaaaa ctcatctcag   2700
aagaggatct gaatggggcc gcatagggtt ccggtgattt tgattatgaa aagatggcaa   2760
acgctaataa gggggctatg accgaaaatg ccgatgaaaa cgcgctacag tctgacgcta   2820
aaggcaaact tgattctgtc gctactgatt acggtgctgc tatcgatggt ttcattggtg   2880
acgtttccgg ccttgctaat ggtaatggtg ctactggtga ttttgctggc tctaattccc   2940
aaatggctca gtcggtgac  ggtgataatt ccctttaat gaataatttc cgtcaatatt   3000
taccttccct ccctcaatcg gttgaatgtc gcccttttgt ctttagcgct ggtaaaccat   3060 atgaatttc  tattgattgt gacaaaataa acttattccg tggtgtcttt gcgtttcttt   3120
tatatgttgc caccttatg tatgtatttt ctacgtttgc taacatactg cgtaataagg   3180
agtcttaata agaattcact ggccgtcgtt ttacaacgtc gtgactggga aaaccctggc   3240
gttacccaac ttaatcgcct tgcagcacat cccccttcg ccagctggcg taatagcgaa   3300
gaggcccgca ccgatcgccc ttcccaacag ttgcgcagcc tgaatggcga atggcgcctg   3360
atgcggtatt ttctccttac gcatctgtgc ggtatttcac accgcatatg aaaattgtaa   3420
gcgttaatat tttgttaaaa ttcgcgttaa attttgttaa atcagctca ttttttaacc   3480 aataggccga atcggcaaa  atcccttata aatcaaaaga atagaccgag atagggttga   3540
gtgttgttcc agtttggaac aagagtccac tattaaagaa cgtggactcc aacgtcaaag   3600
ggcgaaaaac cgtctatcag ggcgatggcc cactacgtga accatcaccc taatcaagtt   3660
ttttggggtc gaggtgccgt aaagcactaa atcggaaccc taaagggagc cccgatttta   3720
gagcttgacg gggaaagccg gcgaacgtgg cgagaaagga agggaagaaa gcgaaaggag   3780
cgggcgctag ggcgctggca agtgtagcgg tcacgctgcg cgtaaccacc acaccgccg   3840 cgcttaatgc gccgctacag ggcgcgtccc atatggtgca ctctcagtac aatctgctct   3900
gatgccgcat agttaagcca gccccgacac ccgccaacac ccgctgacgc gccctgacgg   3960
gcttgtctgc tcccggcatc cgcttacaga caagctgtga ccgtctccgg gagctgcatg   4020
tgtcagaggt tttcaccgtc atcaccgaaa cgcgcga                            4057
```

The invention claimed is:

1. An antibody capable of binding to a norovirus, wherein the antibody includes any one of amino acid sequences selected from the group consisting of the amino acid sequences represented by SEQ ID NO: 38-SEQ ID NO: 43.

2. The antibody according to claim 1, wherein the norovirus is of GII/4-type.

3. A composite containing:
an antibody according to claim 1,
wherein
the antibody is bound to at least one selected from the group consisting of a solid phase support and a labeled substance.

4. The composite according to claim 3, wherein
the antibody is bound to the solid phase support; and
the solid phase support is selected from the group consisting of a plate, a bead, a disk, a tube, a filter, and a film.

5. The composite according to claim 3, wherein
the antibody is bound to the labeled substance; and
the labeled substance is selected from the group consisting of a fluorescent substance, a luminescent substance, a dye, an enzyme, and a radioactive substance.

6. A detection device comprising:
a composite according to claim 3; and
a detector;
wherein
the detector detects a change of a physical amount based on an antigen-antibody reaction of the composite and the norovirus which is contained in an analyte.

7. The detection device according to claim 6, wherein
the physical amount is selected from the group consisting of luminescence intensity, chromaticity, light transmission, turbidness, absorbance, and radiation dose.

8. A detection method comprising:
(a) bringing a composite according to claim 3 into contact with an analyte; and
(b) detecting a change of a physical amount based on an antigen-antibody reaction of the composite and the norovirus which is contained in the analyte.

9. The detection method according to claim 8, wherein
the physical amount is selected from the group consisting of luminescence intensity, chromaticity, light transmission, turbidness, absorbance, and radiation dose.

* * * * *